US009334476B2

(12) United States Patent
Arinzeh et al.

(10) Patent No.: US 9,334,476 B2
(45) Date of Patent: May 10, 2016

(54) METHOD FOR NERVE GROWTH AND REPAIR USING A PIEZOELECTRIC SCAFFOLD

(75) Inventors: Treena Arinzeh, West Orange, NJ (US); George Collins, Maplewood, NJ (US); Yee-Shuan Lee, Kearny, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 841 days.

(21) Appl. No.: 12/661,264

(22) Filed: Mar. 12, 2010

(65) Prior Publication Data
US 2010/0324697 A1 Dec. 23, 2010

Related U.S. Application Data

(63) Continuation-in-part of application No. 12/411,320, filed on Mar. 25, 2009.

(60) Provisional application No. 61/159,751, filed on Mar. 12, 2009.

(51) Int. Cl.
C12N 5/079 (2010.01)
A61L 27/16 (2006.01)
A61L 27/54 (2006.01)
C12N 5/00 (2006.01)
C12M 1/12 (2006.01)

(52) U.S. Cl.
CPC .............. *C12N 5/0618* (2013.01); *A61L 27/16* (2013.01); *A61L 27/54* (2013.01); *C12N 5/0068* (2013.01); *A61L 2300/414* (2013.01); *A61L 2400/12* (2013.01); *C12M 25/14* (2013.01); *C12N 2533/30* (2013.01)

(58) Field of Classification Search
CPC ............ A61N 1/36032; A61N 1/0541; A61N 1/0551; A61N 1/36139; A61N 1/0531; A61N 1/36071; A61N 1/0529; A61N 1/0534; A61N 1/0553; A61N 1/08; A61N 1/36103; A61N 1/36125; A61N 1/3718; A61N 1/37264; A61N 1/375; A61N 2001/086; C12N 5/0068; C12N 11/08; C12N 13/00; C12N 2500/30; C12N 2500/44; C12N 2500/90; C12N 2501/125; C12N 2501/23; C12N 2529/00; C12N 2533/30; C12N 2535/00; C12N 5/0647; C12N 5/0662; C12N 5/0682
See application file for complete search history.

(56) References Cited

U.S. PATENT DOCUMENTS

| 5,353,498 A | 10/1884 | Eillion et al. |
| 4,846,835 A | 7/1989 | Grande |
| 5,030,225 A * | 7/1991 | Aebischer et al. ............ 606/152 |
| 5,250,843 A | 10/1993 | Eichelberger |
| 5,486,359 A | 1/1996 | Caplan |
| 5,522,879 A | 6/1996 | Scopelianos |
| 5,626,861 A | 5/1997 | Laurencin et al. |
| 5,666,467 A * | 9/1997 | Colak ............................. 706/33 |
| 5,681,873 A | 10/1997 | Norton et al. |
| 5,766,618 A | 6/1998 | Laurencin et al. |
| 5,811,094 A | 9/1998 | Caplan |
| 5,827,735 A | 10/1998 | Young |
| 5,841,193 A | 11/1998 | Eichelberger |
| 5,906,934 A | 5/1999 | Grande et al. |
| 5,955,529 A | 9/1999 | Imai et al. |
| 6,095,148 A * | 8/2000 | Shastri et al. ................. 128/898 |
| 6,165,486 A | 12/2000 | Marra et al. |
| 6,174,333 B1 | 1/2001 | Kadiyala |
| 6,214,369 B1 | 4/2001 | Grande et al. |
| 6,306,424 B1 | 10/2001 | Vyakarnam |
| 6,355,239 B1 | 3/2002 | Bruder |
| 6,387,367 B1 | 5/2002 | David-Sproul |
| 6,464,983 B1 | 10/2002 | Grotendorst |
| 6,472,210 B1 | 10/2002 | Holy et al. |
| 6,482,231 B1 | 11/2002 | Abatangelo |
| 6,489,165 B2 | 12/2002 | Bhatnagar et al. |
| 6,511,511 B1 | 1/2003 | Slivka et al. |
| 6,541,024 B1 | 4/2003 | Kadiyala |
| 6,685,956 B2 | 2/2004 | Chu |
| 6,689,166 B2 | 2/2004 | Laurencin et al. |
| 6,689,374 B2 | 2/2004 | Chu |
| 6,730,252 B1 | 5/2004 | Teoh et al. |
| 6,783,712 B2 | 8/2004 | Slivka et al. |
| 6,790,455 B2 | 9/2004 | Chu |
| 6,790,528 B2 | 9/2004 | Wendorff et al. |
| 6,863,900 B2 | 3/2005 | Kadiyala |

(Continued)

FOREIGN PATENT DOCUMENTS

| WO | WO 2006/068809 | 6/2006 |
| WO | WO 2006/095021 A1 | 9/2006 |
| WO | WO 2008/055038 A2 | 5/2008 |

OTHER PUBLICATIONS

Davis, et al., Structural and Dielectric Investigation on the Nature of the Transition in a Copolymer of Vinylidene Fluoride and Trifluoroethylene, Macromolecules, 15: 329-333, 1982.
Lovinger, Ferroelectric Polymers, Science, New Series, vol. 220, No. 4602, pp. 1115-1121, 1983.
Petel, et al., Perturbation of the Direction of Neurite Growth by Pulsed and Focal Electric Fields, Journal of Neurosci, vol. 4, pp. 2939-2947, 1984.
Sambrook et al., Molecular Cloning: A Laboratory Manual, $2^{nd}$ 3d., Cold Spring Harbor Laboratory, Cold Spring Harbor Laboratory Press, Cold Spring Harbor, NY, 1989. (cover page and Table of Contents for vols. 1-3).

(Continued)

*Primary Examiner* — Blaine Lankford
(74) *Attorney, Agent, or Firm* — McCarter & English, LLP

(57) ABSTRACT

Provided is an electroactive structure for growing isolated differentiable cells comprising a three dimensional matrix of fibers formed of a biocompatible synthetic piezoelectric polymeric material, wherein the matrix of fibers is seeded with the isolated differentiable cells and forms a supporting scaffold for growing the isolated differentiable cells, and wherein the matrix of fibers stimulates differentiation of the isolated differentiable cells into a mature cell phenotype on the structure.

3 Claims, 9 Drawing Sheets

(56) References Cited

U.S. PATENT DOCUMENTS

| | | | |
|---|---|---|---|
| 7,012,106 B2 | 3/2006 | Yuan et al. | |
| 7,022,522 B2 | 4/2006 | Guan et al. | |
| 7,247,313 B2* | 7/2007 | Roorda et al. | 424/423 |
| 7,271,234 B2* | 9/2007 | Kohn et al. | 528/196 |
| 7,601,525 B2* | 10/2009 | Batich et al. | 435/178 |
| 7,619,901 B2 | 11/2009 | Eichelberger et al. | |
| 7,767,221 B2 | 8/2010 | Lu et al. | |
| 7,803,574 B2* | 9/2010 | Desai et al. | 435/41 |
| 2002/0004039 A1* | 1/2002 | Reid et al. | 424/93.7 |
| 2002/0034796 A1 | 3/2002 | Shastri et al. | |
| 2002/0173213 A1 | 11/2002 | Chu et al. | |
| 2003/0054035 A1 | 3/2003 | Chu et al. | |
| 2003/0069369 A1 | 4/2003 | Belenkaya et al. | |
| 2003/0077311 A1 | 4/2003 | Vyakarnam et al. | |
| 2003/0211130 A1 | 11/2003 | Sanders et al. | |
| 2004/0018226 A1 | 1/2004 | Wnek et al. | |
| 2005/0095695 A1 | 5/2005 | Shindler et al. | |
| 2005/0196423 A1* | 9/2005 | Batich et al. | 424/423 |
| 2006/0057377 A1 | 3/2006 | Harrison et al. | |
| 2006/0094320 A1 | 5/2006 | Chen et al. | |
| 2006/0128012 A1 | 6/2006 | Arinzeh | |
| 2006/0198865 A1 | 9/2006 | Freyman et al. | |
| 2006/0204539 A1 | 9/2006 | Atala et al. | |
| 2006/0240064 A9 | 10/2006 | Hunter et al. | |
| 2007/0179594 A1 | 8/2007 | Llanos et al. | |
| 2007/0267725 A1 | 11/2007 | Lee et al. | |
| 2008/0009599 A1 | 1/2008 | East et al. | |
| 2008/0112150 A1 | 5/2008 | Jones | |
| 2008/0206343 A1* | 8/2008 | Edinger et al. | 424/489 |
| 2008/0246126 A1 | 10/2008 | Bowles et al. | |
| 2009/0028921 A1 | 1/2009 | Arinzeh | |
| 2009/0048358 A1 | 2/2009 | Kim | |
| 2009/0325296 A1* | 12/2009 | Arinzeh et al. | 435/396 |
| 2010/0078771 A1 | 4/2010 | Barth et al. | |
| 2010/0078776 A1 | 4/2010 | Barth et al. | |
| 2010/0173158 A1 | 7/2010 | Furuzono et al. | |
| 2010/0233807 A1 | 9/2010 | Arinzeh et al. | |
| 2010/0324697 A1* | 12/2010 | Arinzeh et al. | 623/23.72 |

OTHER PUBLICATIONS

Borgens, Electric Fields in Vertebrate Repair, Natural and Applied Voltage in Vertebrate Regeneration and Healing, Wiley-Liss, 1989.
Safronova, et al., Characteristics of the Macromolecular Components of the Extracellular Matrix in Human Hyaline Cartilage at Different Stages of Ontogenesis, Biomedical Science, 2:162-168, 1991.
Valentini, Electrically Charged Polymeric Substrates Enhance Nerve-Fiber Outgrowth in Vitro, Biomaterials, vol. 13, pp. 183-190, 1992.
Ausubel, et al., Current Protocols in Molecular Biology, John Wiley & Sons, New York, NY, 1993. (cover page and Table of Contentst).
Kapur, et al, J, Biomed Mater. Res., 32: 133, 1996 (abstract only).
Humphrey, et al., The Dielectric Piezoelectric and Pyroelectric Properties of VDF-TrFE Copolymers, Plessey Research (Caswell) Limited, Allen Clark Research Centre, Caswell, Towcester, Northants, NN12 8EQ, England, 1986.
Koga, et al., Crystallization, Field-Induced Phase Transformation, Thermally Induced Phase Transition, and Piezoelectric Activity in P(Vinylidene Fluoride-TrFE) Copolymers with High Molar Content of Vinylidene Fluoride, J. Appl. Phys, 67(2), pp. 965-974, 1990.
Ohigashi, et al., Formation of "Single Crystalline Films" of Ferroelectric Copolymers of Vinylidene Fluoride and Trifluoroethylene, Appl. Phys. Lett., 66(24), pp. 3281-3283, 1995.
Kapur., et al., Fabrication and Selective Surface Modification of 3-Dimensionally Textured Biomedical Polymers from Etched Silicon Substrates, Journal of Biomedical Materials Research, vol. 33, pp. 205-216 (1996).
Omote, et al., Temperature Dependence of Elastic, Dielectric, and Piezoelectric Properties of "Single Crystalline" Films of Vinylidene Fluoride Trifluoroethylene Copolymer, J. Appl. Phys., 81(6), pp. 2760-2769, 1997.
Christie, et al., Ferroelectric and Piezoelectric Properties of a Quenched Poly(Vinylidene Fluoride-Trifluoroethylene) Copolymer, Journal of Polymer Science: Part B: Polymer Physics, vol. 35, 2671-2679, 1997.
Borgens, Electrically Mediated Regeneration and Guidance of Adult Mammalian Spinal Axons into Polymeric Channels, Neuroscience, 91(1):251-64; 1999.
Schmidt, et al., Stimulation of Neurite Outgrowth Using an Electrically Conducting Polymer, Proc. Natl. Acad. Sci, vol. 94, pp. 8948-8953, 1997.
Furukawa, Structure and Functional Properties of Ferroelectric Polymers, Advances in Colloid and Interface Science, 71-72; 183-208, 1997.
Bouaziz, et al., Vascular Endothelial Cell Responses to Different Electrically Charged Poly(Vinylidene Fluoride) Supports Under Static and Oscillating Flow Conditions, Biomaterials, vol. 18, No. 2, 107-112, 1997.
Bune, et al., Two-Dimensional Ferroelectric Films, Nature, vol. 391, 874-877, 1998.
Zhao, et al., Electromechanical Properties of Electrostrictive Poly(Vinylidene Fluoride-Trifluoroethylene) Copolymer, Applied Physics Letters, vol. 73, No. 14, pp. 2054-2056, 1998.
Fuchs, et al., Stem Cells: A New Lease on Life, Cell 100: 143-155 (2000).
Watt , et al., Out of Eden: Stem Cells and Their Niches, Science 287:1427-1430 (2000).
DeLise, et al., Cellular Interactions and Signaling in Cartilage Development, Osteoarthritis and Cartilage, 8: 309-334 (2000).
Ponticello et al., Gelatin-Based Resorbable Sponge As a Carrier Matrix for Human Mesenchymal Stem Cells in Cartilage Regeneration Therapy, J Biomed Materials Res 52: 246-255 (2000).
Hilczer, et al., The Method of Matching Resonance Frequencies in Coupled Transmitter PVDF/TRFE Diaphragms, IEEE Transactions on Dielectrics and Electrical Insulation, vol. 7, No. 4, pp. 498-502, 2000.
Xie, et al., A Niche Maintaining Germ Line Stem Cells in Drosophila Ovary, Science 290:328-330, 2000.
N.S.C.I.A., Spinal Cord Injury Fact Sheet, Birmingham, 2001; http://users.erols.com/nscia/resource/factshts/.
Yannas IV, Tissue and Organ Regeneration in Adults, Springer, 2001(cover page and Table of Contents).
Kotwal, et al., Electrical Stimulation Alters Protein Adsorption and Nerve Cell Interactions With Electrically Conducting Biomaterials, Biomaterials, 22: 1055-1064, 2001.
Koombhongse, et al., Flat Polymer Ribbons and Other Shapes by Electrospinning, Journal of Polymer Science: Part B: Polymer Physics, vol. 39, 2598-2606, 2001.
Ploss, et al., Poling Study of PZT/P(VDF-TrFE) Composites, Composites Science and Technology, 61, 957-962, 2001.
Harrison, et al., Piezlelectric Polymers, ICASE, NASA Langley Research Center, Hampton, Virginia, NASA/CR-2001-211422, ICASE Report No. 2001-43, pp. 1-26, 2001.
Brook et al., Columns of Schwann Cells Extruded Into the CNS Induce In-Growth of Astrocytes to Form Organized New Glial Pathways, GLIA, 33:118-130, 2001.
Negishi, Optic Nerve Regeneration Within Artificial Schwann Cell Graft in the Adult Rat, Brain Research Bulletin, 55:409-419, 2001.
Barry, et al., Chondrogenic Differentiation of Mesenchymal Stem Cells from Bone Marrow: Differentiation-Dependent Gene Expression of Matrix Components, Experimental Cell Research, 268:189-200 (2001).
Mueller, et al., Processing of Gene Expression Data Generated by Quantitative Real-Time RT-PCR, BioTechniques, 32: No. 6, 2-7 (2002).
Murphy et al., Stem Cell Therapy in a Caprine Model of Osteoarthritis, Arthritis Rheumatism 48: No. 12, 3464-3474 (2003).
Sachlos, et al., Making Tissue Engineering Scaffolds Work, Review of the Application of Solid Freeform Fabrication Technology to the Production of Tissue Engineering Scaffolds, European Cells & Materials 5: 29-40 (2003).

(56) References Cited

OTHER PUBLICATIONS

Livingston, et al., Mesenchymal Stem Cells Combined With Biphasic Calcium Phosphate Ceramics Promote Bone Regeneration, Journal of Materials Science: Materials in Medicine, 14: 211-218 (2003).
Li, et al., Biological Response of Chondrocytes Cultured in Three-Dimensional Nanofibrous Poly(e-caprolactone) Scaffolds, J. Biomed. Mater. Res. 67A: 1105-1114 (2003).
Wan-Ju, et al., J. Biomed. Mater. Res. 67A:1105-1114, 2003.
Rosenzweig, et al., Rodent Models for Treatment of Spinal Cord Injury: Research Trends and Progress Toward Useful Repair, Current Opinion in Neurology, 17(2); 121-31, 2004.
Desawa, Specific Induction of Neuronal Cells From Bone Marrow Stromal Cells and Application for Autologous Transplantation, Journal of Clinical Investigation; 113:1701-1710, 2004.
Benz, et al., Determination of the Crystalline Phases of Poly(Vinylidene Fluoride) Under Different Preparation Conditions Using Differential Scanning Calorimetry and Infrared Spectroscopy, Journal of Applied Polymer Science, vol. 89, 1093-1100, 2003.
Seoul, et al., Electrospinning of Poly(Vinylidene Fluoride)/Dimethylformamide Solutions With Carbon Nanotubes, Journal of Polymer Science: part B: Polymer Physics, vol. 41, 1572-1577, 2003.
Bryan, et al., Enhanced Peripheral Nerve Regeneration Through a Poled Bioresorbable Poly(Lactic-co-glycolic Acid) Guidance Channel, J. Neural Eng., 1, 91-98, 2004.
Zhao, et al., Preparation and Properties of Electrospun Poly(Vinylidene Fluoride) Membranes, Journal of Applied Polymer Science, vol. 97, 466-474, 2005.
Zhang et al., Tissue-Engineering Approaches for Axonal Guidance, Brain Res. Brain Res. Rev, vol. 49, pp. 48-64, 2005.
Naber, et al., Low-Voltage Programmable Ferroelectric Polymer Field-Effect Transistors, Applied Physics Letters, 87: 203509, pp. 51-57, 2005.
Ducharme, et al., Ferroelectric Polymeric Langmuir-Blodgett Films for Non-Volatile Memory Applications, Nebraska Research Initiative, the National Science Foundation and the Office of Naval Research, Department of Physics and Astronomy and the Center for Materials Research and Analysis at the University of Nebraska, Lincoln, NE, pp. 1-41, 2005.
Klein, et al., Influence of Composition on Relaxor Ferroelectric and Electromechanical Properties of Poly(Vinyliden Fluoride-Trifluoroethylene-Chlorofluoroethylene), Journal of Applied Physics, 97, 094105, pp. 1-4, 2005.
Laxminarayana, et al., Functional Nanotube-Based Textiles: Pathyway to Next Generation Fabrics With Enhanced Sensing Capabilities, Textile Res. J., 75(9), 670-680, 2005.
Cummings, et al., Human Neural Stem Cells Differentiate and Promote Locomoter Recovery in Spinal Cord-Injured Mice, Proceedings of the National Academy of Sciences, 102(39):14069-74, 2005.
Shapiro, et al., Oscillating Field Stimulation for Complete Spinal Cord Injury in Humans: A Phase 1 Trial, Journal of Neurosurgery Spine, 2005:2(1):3-10.
Himes, et al., Recovery of Function Following Grafting of Human Bone Marrow-Derived Stromal Cells Into the Injured Spinal Cord, Neurorehabilitation and Neural Repair, 20:278-96, 2006.
Cizkova, et al., Transplants of Human Mesenchymal Stem Cells Improve Functional Recovery After Spinal Cord Injury in the Rat, Cellular and Molecular Neurobiology, 26(7/8):1167-80, 2006.
Nasir, et al., Control of Diameter, Morphology, and Structure of PVDF Nanofiber Fabricated by Electrospray Deposition, Journal of Polymer Science: Part B: Polymer Physics, vol. 44, 779-786, 2006.
Beloti, et al., In Vitro Biocompatibility of a Novel Membrane of the Composite Poly(Vinylidene-Trifluoroethylene)/Barium Titanate, InterScience Journal of Biomedical Materials Research Part A, 281-288, 2006.
Hung, et al., The Effect of Chitosan and PVDF Substrates on the Behavior of Embryonic Rat Cerebral Cortical Stem Cells, Biomaterials, 27, 4461-4469, 2006.
Wu, et al., Poly(Vinylidene Fluoride)/Polyethersulfone Blend Membranes: Effects of Solvent Sort, Polyethersulfone and Polyvinylpyrrolidone Concentration on Their Properties and Morphology, Journal of Membrane Science, 285, 290-298, 2006.
Yang, et al., Preparation of Bioelectret Collagen and Its Influence on Cell Culture In Vitro, J. Mater. Sci: Mater Med, 17:767-771, 2006.
Tashiro, et al, Structural Correlation Between Crystal Lattice and Lamellar Morphology in the Ferroelectric Phase Transition of Vinylidene Fluoride-Trifluoroethylene Copolymers as Revealed by the Simultaneous Measurements of Wide-Angle and Small-Angle X-Ray Scatterings, Polymer, 47, 5433-5444, 2006.
Yang, et al., Preparation of Bioelectret Collagen and its Influencen on Cell Culture in vitro, Journal Material Science Mater. Med. 17: 767-771 (2006).
Li et al., Electrospinning Polyaniline-Contained Gelatin Nanofibers for Tissue Engineering Applications, Biomaterials, vol. 27, pp. 2705-275, 2006.
Oudega, et al., Schwann Cell Transplantation for Repair of the Adult Spinal Cord, Journal of Neurotrauma, 23(3-4), 453-67, 2006.
Catalani, et al., Evidence for Molecular Orientation and Residual Charge in the Electrospinning of Poly (Butylenes Terephthalate) Nanofibers, Macromolecules, vol. 40, pp. 1693-1697, 2007.
Wi, et al., Characterization of Poly(Vinylidene Fluoride-Trifluoroethylene) 50/50 Copolymer Films as a Gate Dielectric, J. Mater Sci: Mater Electron, pp. 1-6, 2007.
Greiner, et al, Electrospinning: A Fascinating Method for the Preparation of Ultrathin Fibers, Angewandte Chemie Int. Ed. Engl. 46: 5670-5703 (2007).
Kim, et al., The Role of Aligned Polymer Fiber-Based Constructs in the Bridging of Long Peripheral Nerve Gaps, Biomaterials, 29(21):3117-27, 2008.
Lankford, et al., Olfactory Ensheathing Cells Exhibit Unique Migratory, Phagocytic and Myelinating Properties in the X-Irradiated Spinal Cord Not Shared by Schwann Cells, Glia, 2008; epub ahead of print.
Duffell., et al., Long-Term Intensive Electrically Stimulated Cycling by Spinal Cord-Injured People: Effect on Muscle Properties and Their Relation to Power Output, Muscle and Nerve, 2008, 38:1304-11.
http://stemcells.nih.gov/info/scireport/appendixE.asp, (visited Dec. 28, 2007; last visited Aug. 25, 2011), 6 pages.
Hardingham, Proteoglycans: Their Structure, Interactions and Molecular Organization in Cartilage, Biochemical Society Transactions, vol. 9, No. 6, pp. 489-497, 1981.
Friedenstein, A. et al., Bone Marrow Osteogenetic Stem Cells: In Vitro Cultivation and Transplantation in Diffusion Chambers, Cell Tissue Kinet, 20(3):263-72, 1987.
Haynesworth, S. et al., Cell Surface Antigens on Human Marrow-Derived Mesenchymal Stem Cells are Detected by Monoclonal Antibodies, J. Cell Physiol., 138:8-16, 1992.
Rickard, D. J. et al., Induction of rapid osteoblast differentiation in rat bone marrow stromal cell cultures by dexamethason and BMP-2, Dev. Bio., 161:218-28, 1994.
Kapur., et al., Fabrication and Selective Surface Modification of 3-Dimensionally Textured Biomedical Polymers from Etched Silicon Substrates, Journal of Biomedical Materials Research, vol. 33, pp. 205-216, 1996.
Jaiswal, N. et al., Osteogenic differentiation of purified culture-expanded human mesenchymal stem cells in vitro, J. Cell Biochem., 64:295-312, 1997.
Kadiyala, S. et al., Culture-expanded, bone marrow-derived mesenchymal stem cells can regenerate a critical-sized segmental bone defect, Tissue Engineering, 3(2):173-185, 1997.
Miraglia, S. "A Novel Five-Transmembrane Hematopoietic Stem Cell Antigen: Isolation, Characterization, and Molecular Cloning," Blood 90:5013-21, 1997.
Virts, E. et al. "Murine Mast Cells and Monocytes Express Distinctive Sets of CD45 Isoforms," Immunology 34(16-17):1119-97, 1997.
Yin, A.H. "AC133, A Novel Marker for Human Hematopoietic Stem and Progenitor Cells," Blood 90:5002-12, 1997.
Bruder, S. P. et al., Bone Regeneration by Implantation of Purified, Culture-Expanded Human Mesenchymal Stem Cells, J. Orthop. Res., 16:155-162, 1998.

(56) References Cited

OTHER PUBLICATIONS

MacKay, A. M. et al., Chrondrogenic differentiation of cultured human mesenchymal stem cells from marrow, Tissue Engineering, 4(4):415-428, 1998.
Laurencin, C.T. "Tissue Engineering: Orthopedic Applications," Ann. Rev. Biomed. Eng'g 1:19-46, 1999.
Pittenger, M. F. et al., Multilineage potential of adult human mesenchymal stem cells, Science, 284:143-7, 1999.
Praemer, A., Musculoskeletal conditions in the United States, American Academy of Orthopaedic Surgeons, p. 34-39, 1999.
Sittinger et al., Joint cartilage regeneration by tissue engineering, Z. Rheumatol, 58:130-5, 1999.
Browne, J. E. et al., Surgical alternatives for treatment of articular cartilage lesions, J. Am. Acad. Orthop. Surg., 8(3):180-9, 2000.
Christensen, N. D. et al., Papillomavirus microbicidal activities of high-molecular-weight cellulose sulfate, dextran sulfate, and polystyrene sulfonate, Antimicrobial Agents and Chemotherapy, 45(12):3427-32, 2001.
Guo et al., Biological features of mesenchymal stem cells from human bone marrow, Chinese Med J.. 114:950-3, 2001.
Ishihara, M. et al., Heparin-carrying polystyrene (HCPS)-bound collagen substratum to immobilize heparin-binding growth factors and to enhance cellular growth, J. Biomed. Mat. Res., 56(4):536-44, 2001.
Rahman et al., Enhancement of Chondrogenic Differentiation of Human Articular Chondrocytes by Biodegradable Polymers, Tissue Engineering, 7:781-90, 2001.
Rogovina, S. Z. et al., Solid state production of cellulose-chitosan blends and their modification and the diglycidyl ether of oligo(ethylene oxide), Polymer Degradation and Stability, 73(3):557-60, 2001.
Anderson, R. A. et al., Preclinical evaluation of sodium cellulose sulfate (Ushercell) as a contraceptive antimicrobial agent, Journal of Andrology, 23(3):426-38, 2002.
Arinzeh, T. et al.,In vivo evaluation of a bioactive scaffold for bone tissue engineering, J. Biomed. Mat. Res., 62:1-13, 2002.
Dozin, B. et al., Response of young, aged and osteoarthritic human articular chondrocytes to inflammatory cytokines: molecular and cellular aspects, Matrix Biology, 21(5):449-59, 2002.
Li et al., Electrospun Naofibrous Structure: A Novel Scaffold for Tissue Engineering, Journal of Biomedical Materials Research, vol. 60, No. 4, pp. 613-621, 2002.
Nettles et al., Potential Use of Chitosan as a Cell Scaffold Material for Carilage Tissue Engineering, Tissue Engineering, Vo.. 8, No. 6, pp. 1009-1016, 2002.
Arinzeh, T. et al, Allogeneic mesenchymal stem cells regenerate bone in a critical-sized canine segmental defect, Journal of Bone and Joint Surgery American, 85-A(1):1927-35, 2003.
Endres et al., Osteogenic Induction of Human Bone Marrow-Derived Mesenchymal Progenitor Cells in Novel Synthetic Polymer-Hydrogel Matrices, Tissue Engineering, vol. 9, No. 4, pp. 689-702, 2003.
Luu et al., "Development of a Nanostructured DNA Delivery Scaffold via Electrospinning of PLGA and PLA-PEG block copolymers", Journal of Controlled Release, vol. 89, pp. 341-353, 2003.
Sikavitsas et al., "Mineralized Matrix Deposition by Marrow Stromal Osteoblasts in 3D Perfusion Culture Increases With Increasing Fluid Shear Forces". PNAS, vol. 100, No. 25, pp. 14683-14688, Dec. 9, 2003.
Yeh, E.T.H. et al., "Transdifferentiation of Human Peripheral Blood CD34+-Enriched Cell Population Into Cardiomyocytes, Endothelial Cells, and Smooth Muscle Cells in Vivo," Circulation 108:2070-73, 2003.
Yoshimoto et al., A Biodegradable Nanofiber Scaffold by Electrospinning and its Potential for Bone Tissue Engineering, Biomaterials, 24, pp. 2077-2082, 2003.
Zong et al., Electrospun Non-woven Membranes As Scaffolds for Heart Tissue Constructs. 226$^{th}$ ACS National Meeting, 2003.
Bhattarai, et al., Novel Biodegradable Electrospun Membrance: Scaffold for Tissue Engineering, Biomaterials, vol. 25, No. 13, pp. 2595-2602, 2004.
Jin et al., "Human Bone Marrow Stromal Cell Responses on Electrospun Silk Fibroin Mats", Biomaterials, vol. 25, pp. 1039-1047, 2004.
Li et al., Carbon Nanotubes Induced Nonisothermal Crystallization of Ethylene-Vinyl Acetate Copolymer, Materials Letter, 58, pp. 3967-3970, 2004.
Shanmugasundaram, et al., Applications of Electrospinning: Tissue Engineering Scaffolds and Drug Delivery System, Bioengineering, Proceedings of the Northeast Conference, vol. 30, pp. 140-141, 2004.
Shields, K. J. et al., Mechanical properties and cellular proliferation of electrospun collagen Type II, Tissue Engineering, 10(9-10):1510-7, 2004.
Shin et al., In Vivo Bone Tissue Engineering Using Mesenchymal Stem Cells on a Novel Electrospun Nanofibrous Scaffold, Tissue Engineering, 10, pp. 33-41, 2004.
Sittinger et al., Current Strategies for Cell Delivery in Cartilage and Bone Regeneration, Current Opinion in Biotechnology, vol. 115, Issue 5, pp. 411-418, 2004.
Wei et al., Structural and Properties of Nano-Hydroxyapatite/Polymer Composite Scaffolds for Bone Tissue Engineering, Biomaterials, 25, pp. 4749-4757, 2004.
You, J. O. et al., Calcium-alginate nanoparticles formed by reverse microemulsion as gene carriers, macromolecular Symposia, 219(147):153, 2004.
Arinzeh et al., A Comparative Study of Biphasic Calcium Phosphate Ceramics for Human Mesenchymal Stem-Cell-induced Bone Formation, Biomaterials, 26(17): 3631-8, 2005.
Aroen, A. et al, "Articular Cartilage Defects in a Rabbit Model, Retention Rate of Periosteal Flap Cover", Acta Orthrop. 76(2):220-4, 2005.
Browne, J. E. et al., Clinical outcome of autologous chondrocyte implantation at 5 years in US subjects, Clinical Orthopaedics and Related Research, 436:237-45, 2005.
Clar, C. et al., Clinical and cost-effectiveness of autologous chondocyte implantation for cartilage defects in knee joints: systematic review and economic evaluation, Health Technology Assessment, 9(47):four pages, 2005.
Fujihara, et al., Guided Bone Regeneration Membrane Made of Polycaprolactone/Calcium Carbonate Composite Nano-fibers, Biomaterials, 26, pp. 4139-4147, 2005.
Holmes, N. "CD45: All is Not Yet Crystal Clear", Immunology 117:145-155, 2005.
Kang, S. W. et al., Ply(lactic-co-glycolic acid) microspheres as an injectible scaffold for cartilage tissue engineering, Tissue Engineering, 11(3-4):438-47, 2005.
Li et al., Multilineage Differentiation of Human Mesenchymal Stem Cells in a Three-Dimensional Nanofibrous Scaffold, Biomaterials, vol. 26, No. 25, pp. 5158-5166, 2005.
Livingston, et al., A Comparative Study of Biphasic Calcium Phosphate Ceramics for Human Mesenchymal Stem-Cell-Induced Bone Formation, Biomaterials, 26, pp. 3631-3638, 2005.
Maire, M. et al., Retention of transforming growth factor using functionalized dextran-based hydrogels, Biomaterials, 26(14):1771-80, 2005.
Montjovent et al., Biocompatibility of Bioresorbable Poly(L-lactic acid) Composite Scaffolds Obtained by Supercritical Gas Foaming With Human Fetal Bone Cells, Tissue Engineering 11, pp. 1640-1649, 2005.
Schaffellner, S. et al., Porcine islet cells microencapsulated in sodium cellulose sulfate, Transplantation Proceedings, 37(1):248-52, 2005.
Wutticharoenmongkol, et al., Electrospinning of Polystyrene/Poly(2-methoxy-5-(2'-ethylhexyloxy)-1,4-phenylene Vinylene) Blends, Journal of Polymer Science: Part B: Polymer Physics, vol. 43, pp. 1881-1891, 2005.
Wutticharoenmongkol, Preparation and Characterization of Novel Bone Scaffolds Based on Electrospun Polycaprolactone Fibers Filled with Nanoparticles, Macromolecular Bioscience, vol. 6, pp. 70-77, 2005.

(56) References Cited

OTHER PUBLICATIONS

Gama, C. L., Sulfation patterns of glycosaminoglycans encode molecular recognition and activity, Nature Chemical Biology, 2(9):467-73, 2006.

Georgiou et al., Polyactic Acid-Phosphate Glass Composite Foams as Scaffolds for Bone Tissue Engineering, J. Biomed. Mat. Res. Part B: Applied Biomaterials, Published Online Jul. 12, 2006.

Kuo, C. K. et al., Cartilage tissue engineering: its potential and uses, Current Opinion in Rheumatology, 18(1):64-73, 2006.

Pelttari, K. et al., Premature induction of hypertrophy during in vitro chondrogenesis of human mesenchymal stem cells correlates with calcification and vascular invasion after ectopic transplantation in SCID mice, Arthritis and Rheumatism, 54:3254-66, 2006.

Rezwan et al., Biodegradable and Bioactive Porous Polymer/inorganic Composite Scaffolds for Bone Tissue Engineering, Biomaterials, 27, pp. 3413-3431, 2006.

Shanmugasundaram, S. et al., The Effect of Varying the Architecture of Scaffolds on Mesenchymal Stem Cell Osteogenesis and Chondrogenesis, Transactions of the 2006 Annual Meeting of the Society for Biomaterials, 2006.

Stiegler, P. B. et al., Cryopreservation of insulin-producing cells microencapsulated in sodium cellulose sulfate, Transplantation Proceedings, 38(9):3026-30, 2006.

Thomas et al., Electrospun Bioactive Nanocomposite Scaffolds of Polycaprolactone and Nanohydroxyapatite for Bone Tissue Engineering, Journal of Nanoscience Nanotechnology, 6(2), pp. 487-493, 2006.

Wutticharoenmongkol et al., Preparation and Characterization of Novel Bone Scaffolds Based on Electrospun Polycaprolactone Fibers Filled with Nanoparticles, Macromol. Biosci. 6, pp. 70-77, 2006.

Wutticharoenmongkol, et al., Novel Bone Scaffolds of Electrospun Polycaprolactone Fibers Filled With Nanoparticles, Journal of Nanoscience Nanotechnology, 6(2), pp. 514-522, 2006.

Chamberlain, G. et al., Concise review: mesenchymal stem cells: their phenotype, differentiation capacity, immunological features, and potential for homing, Stem Cells, 25(11):2739-49, 2007.

Collins, M. N. et al., Comparison of the effectiveness of four different crosslinking agents with hyaluronic acid hydrogel films for tissue-culture applications, Journal of Applied Polymer Science, 104(5):3183-91, 2007.

Greco, S. et al., An interdisciplinary approach and characterization of neuronal cells transdifferentiated from human mesenchymal stem cells, Stem cells and development, 16(5):811-26, 2007.

Greco, S. J. et al., Functional similarities among genes regulated by oct-4 in human mesenchymal and embryonic stem cells, Stem Cells, 25(12:3143-54, 2007.

Huang, Isothermal Crystallization of High-Density Polyethylene and Nanoscale Calcium Carbonate Composites, Journal of Applied Science, 107, pp. 3163-3172, 2007.

Karlsson, C. et al., Differentiation of human mesenchymal stem cells and articular chondrocytes: analysis of chondrogenic potential and expression pattern of differentiation-related transcription factors, Journal of Orthopaedic Research, 25:152-63, 2007.

Lack, S. et al., High-resolution nuclear magnetic resonance spectroscopy studies of polysaccharides crosslinked by sodium trimetaphosphate: a proposal for the reaction mechanism, Carbohydrate Research, 342(7):943-53, 2007.

Miyazaki, et al., Crystallization Rate of Amorphous Nifedipine Analogues Unrelated to the Glass Transition Temperature, Interational Journal of Pharmaeceutics, 336, pp. 191-195, 2007.

Osiris Therapeutics Announces Positive One Year Data from Chondrogen Trial for Knee Repair, Osiris Therapeutics, Inc., Ref. Type: Internet Communication, 2007.

Sun, et al. Crystallization and Thermal Properties of Polyamide 6 Composites Filled With Different Nanofillers, Materials Letters, 61, pp. 3963-3966, 2007.

Temple, M. M. et al., Age- and site-associate biomechanical weakening of human articular cartilage of the femoral condyle, Osteoarthritis and Cartilage, 15:1042-52, 2007.

Venugopal et al., Biocomposite Nanofibres and Osteoblasts for Bone Tissue Engineering, Nanotechnology, 18, pp. 1-8, 2007.

Xin, X. et al., Continuing differentiation of human mesenchymal stem cells and induced chondrogenic and osteogenic lineages in electrospun PLGA nanofiber scaffold, Biomaterials, 28(2):316-25, 2007.

Zhou et al., In Vitro Bone Engineering Based on Polycaprolactone and Polycaprolactone-Tricalcium Phosphate Composites, Polym. Int. 56, pp. 333-342, 2007.

Bian, L. et al., Influence of chondoitin sulfate on the biochemical, mechanical and frictional properties of cartilage explants in long-term culture, Journal of Biomechanics, In press 2008.

Chen, Y. et al., Development of a chitosan-based nanoparticle formulation for delivery of a hydrophilic hexapeptide, dalargin, Biopolymers, 90(5):663-70, 2008.

Chondrogen clinical trial information for the treatment of knee injuries, Osiris Therapeutics, Inc., Ref. Type: Internet Communication, 2008.

Forsten-Williams, K., et al., Control of growth factor networks by heparin sulfate proteoglycans, Annals of Biomedical Engineering, 36(12):2134-48, 2008.

Liu, Z. et al., Polysaccharides-based nanoparticles as drug delivery systems, Advanced Drug Delivery Reviews, 60(15):1650-62, 2008.

Magnussen, R. A. et al., Treatment of focal articular cartilage defects in the knee: a systematic review, Clinical Orthopaedics and Related Research, 466(4):952-62, 2008.

Mueller, M. B. et al., Functional characterization of hypertrophy in chondrogenesis of human mesenchymal stem cells, Arthritis and Rheumatism, 58(5):1377-88, 2008.

PCT International Search Report and Written Opinion for PCT/US2005/043876 dated Jun. 25, 2008.

PCT International Search Report and Written Opinion for PCT/US2008/067322 dated Sep. 29, 2008.

ISP Dec. 24, 2008 for PCT/US2008/067322.

European Search Report dated Dec. 9, 2009 for PCT/US2005/043876.

IPRP Dec. 22, 2009 for PCT/US2008/067322.

Shanmugasundaram, S. et al., Regulation of human mesenchymal stem cell chondrogenesis by scaffold geometry and mechanical properties, Society for Biomaterials Annual Meeting, 2009.

Shanmugasundaram, et al., Microscale Versus Nanoscale Scaffold Arthitecture for Mesenchymal Stem Cell Chondrogenesis, Tissue Engineering: Part A, vol. 60, No. 00, 1010, pp. 1-10.

PCT International Search Report and Written Opinion for PCT/US2012/050156 dated Feb. 1, 2013.

European Patent Office Action for European Patent Application No. 05852938.9 dated Jul. 1, 2014.

* cited by examiner

Nestin – green
tubulin – red
GFAP – blue
DAPI – blue nuclei

METHOD FOR NERVE GROWTH AND REPAIR USING A PIEZOELECTRIC SCAFFOLD

CROSS-REFERENCE TO RELATED APPLICATIONS

This application is a continuation-in-part of U.S. patent application Ser. No. 12/411,320 filed: Mar. 25, 2009; and claims the benefit under 35 U.S.C. §119(e) of U.S. Provisional Patent Application Ser. No. 61/159,751; filed: Mar. 12, 2009, which are hereby incorporated by reference their entirety.

FIELD OF THE INVENTION

This invention relates to the fields of biotechnology, neuroscience, and regenerative medicine, such as, for example, cell growth/differentiation and/or tissue repair.

BACKGROUND

Nerve injuries, for example, injuries to peripheral, brain, or spinal cord nerves present considerable challenges to repair due to their physiological and morphological complexity. For example, spinal cord injury (SCI) is as any kind of trauma to the spinal cord that results in a loss of function such as movement or sensation. In the United States, there are approximately 250,000 people living with SCI, and 11,000 new injuries are reported every year. (14) Typically, with SCI the neuronal axons are compressed or transected, resulting in tissue damage, cell death, and loss of function. (15) Spinal cord injuries are particularly difficult to treat because the differentiated nerves of the central nervous system demonstrate a diminished capacity for regeneration.

Replacing the damaged tissue with nerves taken from other anatomic sites or allograft material is one option, but the best hope for complete or nearly complete recovery is to coax the damaged nerves to regrow. Schwann cell-laden grafts and nerve conduits have shown promise for repairing nervous tissue (16;17) and optic nerves (18), as have injections of olfactory ensheathing cells (19) and adult stem cells (20), but the size and complexity of the spinal cord warrants the development of specialized constructs.

Local electric fields have been measured during neural development or after nerve injury in various vertebrate systems. In addition, electric fields generated via electrodes can influence neural growth and orientation in vitro (Patel N B. J Neurosci. 1984; 4:2939-47) and have been applied for the treatment of spinal cord injuries in recent clinical trials (Duffell L D. Mus Nerve. 2008; 38: 1304-11).

Therefore, there is an ongoing need for therapeutic approaches with potential to treat and/or ameliorate the effects of nerve injury. Accordingly, compositions and methods that are capable of manipulating local electric fields and promoting cell and tissue growth and/or repair, for example, neuronal cell and tissue growth and/or repair, as presently described, present an opportunity for therapeutic intervention.

SUMMARY

Described herein are compositions and methods useful for promoting the growth and/or differentiation and/or repair of a cell and/or tissue, for example, a differentiable cell such as an isolated stem cell or progenitor cell, e.g., an isolated neuronal stem or progenitor cell, nerve cell or tissue with or without other supporting cells or other progenitor cells.

In certain aspects, the present invention provides an electroactive, or piezoelectric, biomaterial as an electroactive scaffold for facilitating growth, differentiation, and/or repair of a cell and/or a tissue. The piezoelectric material acts as a highly sensitive mechanoelectrical transducer that will generate charges in response to minute vibrational forces. Further provided are piezoelectric compositions comprising a three-dimensional matrix of micro and/or nanofibers of piezoelectric synthetic or biological polymers used as an implantable scaffolding for delivery of differentiable stem/progenitor cells, e.g., human mesenchymal cells, neuronal stem/progenitor cells or the like, in tissue engineering applications and methods of preparing them. The piezoelectric scaffolds, which demonstrate electrical activity in response to minute mechanical deformation, allow the achievement of local electric fields characteristic of the natural extracellular matrix observed during development and regeneration or repair.

In one aspect, the present invention provides an electroactive structure for growing isolated differentiable cells that comprises a three dimensional matrix of micro- and/or nano-sized fibers formed of a biocompatible synthetic piezoelectric polymeric material wherein the matrix of fibers is seeded with the isolated differentiable cells and forms a supporting scaffold for growing the isolated differentiable cells, and wherein the matrix of fibers alone or in combination with other factors stimulates differentiation of the isolated differentiable cells into a mature cell phenotype on the structure. In any of the embodiments described herein, the micro- or nanofibrous matrix of the electroactive structure or scaffold includes a random, and/or aligned, and/or patterned fibrous mesh of fibers.

In other aspects, presently described are polymer scaffolds for promoting tissue growth, differentiation, and/or repair. In an exemplary embodiment of this aspect, the scaffold matrix is comprised of a polymer that demonstrate piezoelectric properties. In certain embodiments, the piezoelectric polymer is a polyvinyl polymer or co-polymer, for example, a permanently piezoelectric poly (vinylidene fluoride trifluoroethylene) (PVDF-TrFE) copolymer.

In another aspect, presently described are polymer scaffolds formed by electrospinning. In an exemplary embodiment of this aspect, the scaffold is comprised of a matrix of micro and/or nanosized fibers formed by electrospinning a piezoelectric polymer (i.e., a polymer that exhibits piezoelectric properties). In certain embodiments, the piezoelectric polymer to be electrospun into fibers comprises a polyvinyl polymer or co-polymer, for example, a permanently piezoelectric poly (vinylidene fluoride trifluoroethylene) (PVDF-TrFE) copolymer. In another embodiment, the matrix fibers are a non-woven mesh of micro- and/or nanosized fibers. In another embodiment, the three dimensional matrix of fibers formed of a biocompatible synthetic piezoelectric polymeric material is formed by electrospinning. In another embodiment, the isolated differentiable cells are multipotent human mesenchymal cells or neuronal stem/progenitor cells.

In certain aspects of the invention, the differentiable cell matures or differentiates within and/or on the scaffold. The differentiation status of a cell can be determined by assessing suitable phenotypic markers, e.g., cell surface proteins, and/or gene expression profiles, which are specific for a differentiated cell. In one embodiment, the mature cell phenotype comprises a neuronal cell phenotype.

In another aspect, the present invention provides a composition for use in tissue engineering that comprises (a) isolated differentiable cells, and (b) a supporting electroactive scaffold for growing the isolated differentiable cells, the supporting scaffold comprising a three dimensional matrix of fibers formed of a biocompatible synthetic piezoelectric polymeric material, wherein the matrix of fibers is seeded with the isolated differentiable cells and forms a supporting scaffold for growing the isolated differentiable cells, and wherein the matrix of fibers stimulates differentiation of the isolated differentiable cells into a mature cell phenotype on the structure. In one embodiment, the biocompatible synthetic piezoelectric polymeric material is poly(vinylidene fluoride trifluoroethylene) copolymer. In another embodiment, the three dimensional matrix of fibers is a non-woven mesh of nanofibers. In still another embodiment, the three dimensional matrix of fibers formed of a biocompatible synthetic piezoelectric polymeric material is formed by electrospinning. In certain embodiments, the isolated differentiable cells are multipotent human mesenchymal cells, or neuronal stem/progenitor cells. In another embodiment, the mature cell phenotype comprises a neuronal cell phenotype. In another embodiment, step (a) further comprises the step of obtaining the differentiable human mesenchymal cells from bone marrow or other tissue, e.g., brain or spine.

In an additional aspect, presently described are polymeric scaffolds for modulating or promoting the growth, differentiation, and/or repair of a cell or tissue, for example, a mesenchymal stem cell, neuronal stem/progenitor cell, neuron, or the like. In certain embodiments, the polymeric scaffolds may include a matrix producing or supporting cell, e.g., a fibroblast. In further aspects, the polymeric scaffolds provided by the invention can be used alone or in combination with a cell to promote repair of damaged tissue, e.g., nerve tissue, in a subject. In certain embodiments, the cell or cells seeded in or on the scaffold comprises a mesnechymal stem cell, a neuronal stem/progenitor cell, a neuron or a combination thereof. In additional embodiments, the polymeric scaffolds are seeded with a matrix producing or supporting cell, e.g., a fibroblast cell, glial cell, or Schwann cell.

In an additional aspect, the polymeric scaffolds provided by the invention are generated or fabricated in order to more closely mimic the structure of the natural extracellular matrix. In an exemplary embodiment of this aspect, the scaffold is comprised of an electrospun polymer that demonstrates piezoelectric properties. In certain embodiments, the electrospun piezoelectric polymer is a polyvinyl polymer or co-polymer, for example, a permanently piezoelectric poly(vinylidene fluoride trifluoroethylene) (PVDF-TrFE) copolymer. In certain embodiments, the PVDF-TrFE is fabricated into a fibrous scaffold and the fibers are random, aligned or a combination of both. In certain embodiments the scaffold matrix, and/or fibers additionally comprise an exogenous protein or compound to promote cell growth, differentiation, and/or repair, including for example, growth factors, chemokines, polysaccharides, glycans, or the like.

In another aspect, described herein are methods for promoting and/or enhancing the growth, differentiation, and/or repair of a cell or of a tissue, e.g., a nerve tissue, comprising seeding a cell on a scaffold comprised of an electrospun polymer that demonstrates piezoelectric properties, wherein the scaffold promotes the growth, differentiation, and/or repair of a cell or tissue within or outside of the scaffold matrix. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer. In certain embodiments, the cell is a mesenchymal stem cell or other progenitor cell, e.g., a neuronal progenitor cell, a neuron, or a combination thereof. In additional embodiments, the cell is seeded together with a matrix producing, and/or supporting cell or progenitor thereof, e.g., a fibroblast, glial cell, and/or Schwann cell.

The preceding general areas of utility are given by way of example only and are not intended to be limiting on the scope of the present disclosure and appended claims. Additional objects and advantages of the present invention will be appreciated by one of ordinary skill in the art in light of the instant claims, description, and examples. For example, the various aspects and embodiments of the invention may be utilized in numerous combinations, all of which are expressly contemplated by the present description. These additional objects and advantages are expressly included within the scope of the present invention.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention.

DETAILED DESCRIPTION

Figure 1:
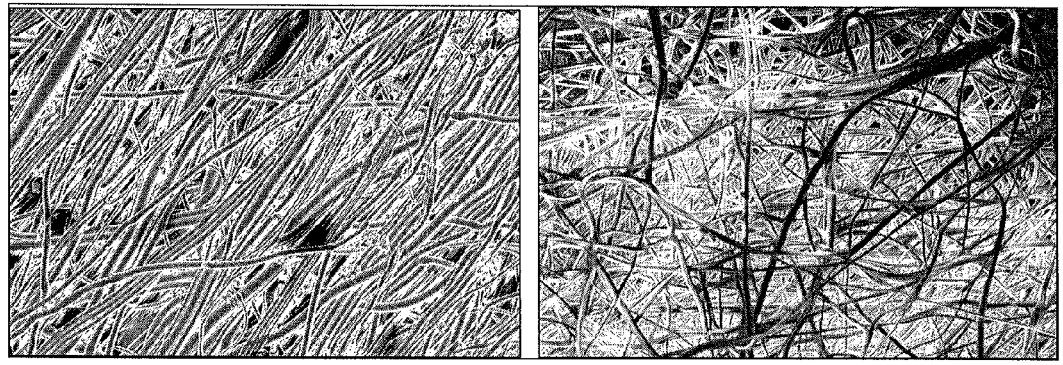
FIG. 1 depicts SEM images (magnification of 3500) of aligned (left) and random (right) electrospun PVDF-TrFE scaffolds.

The following is a detailed description of the invention provided to aid those skilled in the art in practicing the present invention. Those of ordinary skill in the art may make modifications and variations in the embodiments described herein without departing from the spirit or scope of the present invention. Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention. All publications, patent applications, patents, figures and other references mentioned herein are expressly incorporated by reference in their entirety.

Described herein are compositions and methods useful for promoting the growth, differentiation, and/or repair of a cell and/or tissue, e.g., a stem or progenitor cell. In particular, the present invention is based upon the surprising and unexpected discovery that cell and/or tissue growth, differentiation, and/or repair is/are enhanced when grown on a three-dimensional electroactive structure or scaffold comprising microsized or nanosized fibers, or both, of a piezoelectric polymer material. Unless otherwise indicated, the term "polymer" refers to either or both of a homopolymer and heteropolymer (i.e., co-polymer). The compositions and methods provided by the invention are useful as a research tool, a surgical implantation device, a cell or tissue culture device or a combination thereof for in vitro, in vivo, and/or ex vivo culture of a cell and/or tissue, e.g., a stem or progenitor cell, or other cell or tissue for the generation of tissue for repair of damaged tissue, for allographic or xenographic transplantation or any combination thereof.

The following patents and published patent applications are relevant to the subject matter of the present invention: U.S. Pat. Nos. 6,689,166 and 6,790,528; and U.S. Published Pat. App. Nos. 2004-0018226; 2006-0204539; 2009-0325296; 2009-0028921; and 2006-0128012, the disclosures of which are all incorporated herein by reference in their entirety for all purposes.

Unless defined otherwise, all technical and scientific terms used herein have the same meaning as commonly understood by one of ordinary skill in the art to which this invention belongs.

As used herein, the term "stem cell" refers to undifferentiated cells having high proliferative potential with the ability to self-renew that can migrate to areas of injury and can generate daughter cells that can undergo terminal differentiation into more than one distinct cell phenotype. These cells have the ability to differentiate into various cells types and thus promote the regeneration or repair of a diseased or damaged tissue of interest.

The term "progenitor cell" as used herein refers to an immature cell isolated from a tissue, including, e.g., bone marrow, brain, spinal cord, heart, adipose, connective, epithelium, endothelium, or the like, that can be isolated by growing suspensions of the cells in culture dishes with added growth factors. Progenitor cells are referred to as colony-forming units (CFU) or colony-forming cells (CFC). The specific lineage of a progenitor cell is indicated by a suffix, such as, but not limited to, CFU-F (fibroblastic).

As used herein, the term "polymer" refers to a macromolecule formed by the chemical union of five or more identical combining units called monomers. In most cases, the number of monomer is quite large and often is not precisely known. In synthetic polymers, this number may be controlled to a predetermined extent. Combinations two, three, or four monomers are called, respectively, dimers, trimers, and tetramers, and are known collectively as oligomers. Polymers may be inorganic (e.g., siloxane, sulfur chains, black phosphorus, boron-nitrogen, silicones) or organic (meaning containing carbon). Organic polymers may be natural [e.g., polysaccharides, such as starch, cellulose, pectin, seaweed gums, vegetable gums; polypeptides, such as casein, albumin, globulin, keratin, insulin, DNA; and hydrocarbons], synthetic [such as thermoplastics (unvulcanized elastomers, nylon, polyvinyl chloride, poly (vinylidene fluoride trifluoroethylene) linear polyethylene, polystyrene, polypropylene, polyurethane, acrylate resins); thermosetting (e.g., vulcanized elastomers, crosslinked polyethylene, phenolics, alkyds, polyesters), and semisynthetic (e.g., cellulosics, such as rayon, methylcellulose, cellulose acetate; and modified starches)]. The term "homopolymer" refers to a natural or synthetic polymer derived from a single monomer. The term "heteropolymer" refers to a natural or synthetic polymer derived from more than one monomer subunit (i.e., co-polymer). Unless otherwise indicated, the term "polymer" is used generally to refer to both homopolymers and heteropolymers (i.e., co-polymer) as described herein.

The term "cellular differentiation" as used herein refers to the process by which cells acquire a cell type.

The term "ΔHf" refers to Heat of Fusion.

The term "nanoscale fiber" generally refers to fibers whose diameter ranges from about 1 to about 1000 nanometers.

The term "piezoelectric material" as used herein refers to any material that exhibits piezoelectric properties or effects. The terms "piezoelectric properties" or "piezoelectric effects" are used interchangeably to refer to the property exhibited by piezoelectric materials of becoming electrically polarized when mechanically strained and of becoming mechanically strained when an electric field is applied.

The present invention described hereinabove has both human and veterinary utility. The term "subject" as used herein therefore includes animals, e.g., those of mammalian origin, including humans.

The term "Tm" refers to melting point.

The term "growth factor" refers generally to bioactive cell signaling molecules, including cytokines and chemokines, which are known to elicit physiological effects through their interaction with cell surface receptors (typically receptor tyrosine kinases, Ser/Thr kinases, immunoglobulins or GPCRs) on a cell. The physiological effects of growth factor binding to its receptor include, for example, changes in gene expression, and/or cell proliferation, differentiation, activation, quiescence, or apoptosis. In certain cases, growth factors are pleiotropic, i.e., they may induce different physiological effects depending on the concentration, cell type, and/or cell status. In any of the embodiments provided herein, the fiber, matrix, and/or scaffold may additionally include one or more growth factors to enhance, e.g., cell or tissue growth, differentiation, and/or repair.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Although any methods and materials similar or equivalent to those described herein can also be used in the practice or testing of the present invention, the preferred methods and materials are now described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise. All technical and scientific terms used herein have the same meaning.

In certain aspects, the present invention provides an electroactive, or piezoelectric, biomaterial as an electroactive scaffold for enhancing or facilitating growth, differentiation, and/or repair of a cell and/or a tissue. The piezoelectric material acts as a highly sensitive mechanoelectrical transducer that will generate charges in response to minute vibrational forces. In certain embodiments, the invention provides piezoelectric compositions comprising a three-dimensional matrix of micro- and/or nanofibers of piezoelectric synthetic or biological polymers used as an implantable scaffolding for the growth and/or delivery of differentiable cells, for example, mesenchymal stem cells, progenitor cells, including neuronal stem/progenitor cells or any other cell for tissue engineering applications and methods of preparing them. The piezoelectric scaffolds, which demonstrate electrical activity in response to minute mechanical deformation, allow the achievement of local electric fields characteristic of the natural extracellular matrix observed during development and regeneration or repair. The differentiable cells can be isolated according to well known methods and may be isolated from any suitable subject, for example, a mammal, including a human.

Random, aligned, and patterned nano-fibrous mesh and three-dimensional structures can be fabricated by altering collection methods as described herein. The topographic features of nano-aligned-fibrous scaffolds create contact guidance. For example, in the case of a isolated differentiable neuronal stem or progenitor cell, the aligned fibrous scaffold fabricated in accordance with the present description can further facilitate axonal extension. Experimental results have demonstrated for certain exemplary embodiments, enhanced neuronal differentiation and neurite extension on PVDF-TrFe meshes. Also, cells on aligned nanofiber scaffolds extend neurites unidirectionally, parallel with the aligned fibers.

Specialized protein receptors that have the capability of selectively binding or adhering to other signaling molecules coat the surface of every cell in the body. Cells use these receptors and the molecules that bind to them as a way of communicating with other cells and to carry out their proper functions in the body. Each cell type has a certain combination of receptors, or markers, on their surface that makes them distinguishable from other kinds of cells. In certain embodiments, comprising a neuronal stem/progenitor cell, piezoelectric polymers can induce transient change of surface charge without requiring additional energy sources or electrodes and have been shown to yield a higher level of neuronal differentiation and neurite outgrowth of mouse neuroblastoma cells.

Therefore, in one aspect the present invention provides a novel electroactive structure or scaffold to be used to promote growth, differentiation, and/or repair of a differentiable stem/progenitor cell, e.g., a mesenchymal cell or neuronal stem/progenitor cell. As described herein, in an exemplary embodiment, the piezoelectric property of the fiber matrix promotes neurite extension by neuronal stem/progenitor cells incorporated into the piezoelectric scaffold. The piezoelectric scaffold in an aligned nanofibrous format provides the appropriate physical cues to promote axonal regeneration. (8-10) By combining the scaffold with neuronal stem/progenitor cells, the cells may provide the therapeutic benefit of neuroprotection (11) and/or functionally integrate into the spared spinal cord circuitry (e.g. forming new oligodendrocytes and/or neurons) (12;13) to improve therapeutic outcomes.

Thus, in an examplary embodiment, the invention provides an electroactive structure for growing an isolated differentiable stem/progenitor cell comprising a three dimensional matrix of fibers comprising a biocompatible synthetic piezoelectric polymeric material, wherein the matrix of fibers is seeded with at least one isolated differentiable stem/progenitor cell and forms a supporting scaffold for growing the isolated differentiable stem/progenitor cell. In certain embodiments, the isolated differentiable cell is a differentiable neuronal stem/progenitor cell or other cell or progenitor cell capable of being differentiated into a nerve cell. In another embodiment, the matrix of piezoelectric fibers stimulates growth, differentiation, and/or repair of the isolated differentiable neuronal progenitor cell into a mature neuronal cell phenotype on the structure, for example, a peripheral nerve, brain or spinal cord neuron. In this context, it is to be understood that the word "on" is used in broad sense and refers to, and includes, by way of example, cells growing partially or completely "on," "in," "within," and/or "through" the structure.

After spinal cord injury (SCI) unidirectional aligned structure of the axons is disrupted [1] and restoring the original structure is necessary for functional recovery. A tissue-engineered bridging device as described herein is a promising method to guide axonal outgrowth for repair of SCI. However, the cell favors the implantation site more [1], thus appropriate topographic cues within the bridging device may be crucial in successfully guiding axons to extend out of the bridge and to enhance host-implant interaction. As discussed above, local electric fields have been measured during neural development or after nerve injury in various vertebrate systems [2]. Electric fields generated via electrodes have been shown to influence growth and orientation of neurons in vitro [3]. It was surprisingly and unexpectedly discovered that piezoelectric polymers can induce transient change of surface charge without requiring additional energy sources or electrodes and have been shown to yield a higher level of cell growth, differentiation, and repair as exemplified by the observed neuronal differentiation and neurite outgrowth of mouse neuroblastoma cells [4].

In any of the embodiments described herein, the biocompatible synthetic piezoelectric polymer may be comprised of any suitable polymeric material that demonstrates piezoelectric properties. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer. The steric hindrance of the TrFe polymer in PVDF-TrFE forces the copolymer into an all-trans configuration and is considered piezoelectric [5].

In certain embodiments, the piezoelectric polymeric scaffold as described herein is formed by electrospinning. Electrospinning is used to synthesize polymeric tissue engineering scaffolds by applying a high voltage to an ejectable polymer solution. The basic principle behind this process is that an electric voltage sufficient enough to overcome the surface tension of a polymeric solution causes the polymer droplets to elongate so that the polymer is splayed randomly as very fine fibers, which when collected on a grounded metal plate, form a non-woven mat or mesh. Traditionally, electrospinning has yielded non-woven (i.e., mesh) mats (also called matrices and scaffolds) of nanometer sized fiber diameters and nanometer sized pore diameters. However, in order for cells to infiltrate into a scaffold and proliferate, micron sized fiber diameters and micron sized pore diameters are optimal. Since the diameter of a cell is approximately 10 $\mu$m to 20 $\mu$m, pore sizes at the cellular level or above are needed to allow for cell infiltration. In an exemplary embodiment, the matrix fibers comprise a non-woven mesh of random and/or aligned nanofibers or microfibers or a combination thereof.

In certain embodiments, the electrospun fibers have an average fiber diameter of from about 100 nm to about 100 microns. In an additional embodiment, the electrospun fibers have an average fiber diameter of from about 600 nm to about 5 microns. In a preferred embodiment, the electrospun fibers are PVDF-TrFE fibers and have an average fiber diameter of from about 750 microns to about 5 microns.

In certain embodiments, the polymer, e.g., PVDF-TrFE, is fabricated into a fibrous matrix scaffold and the fibers are arranged randomly, substantially or approximately aligned or a combination of both. As used herein, "substantially or approximately aligned" refers to a matrix in which the fibers show more directional uniformity in any desired plane as compared to a "random" fiber matrix. In an exemplary embodiment of this aspect, the scaffold is comprised of a matrix of substantially axially aligned electrospun fibers using a polymer that demonstrates piezoelectric properties. In certain embodiments, the electrospun piezoelectric polymer is a polyvinyl polymer or co-polymer, for example, a permanently piezoelectric poly (vinylidene fluoride trifluoroethylene) (PVDF-TrFE) copolymer.

In any of the embodiments described herein, the fibers of the electroactive structure may be thermally annealed prior to seeding with an isolated differentiable stem/progenitor cell. The annealing step increases the size of the beta phase crystal in the piezoelectric materials, which results in an increase in the piezoelectric property or resulting electrical activity of the material. As described in further detail below, thermal annealing of the matrix fibers results in enhanced piezoelectric characteristics, and/or improved crystal organization. The improved piezoelectric properties of the annealed fibers improves stem/progenitor cell growth, and/or differentiation. In a preferred embodiment, the fibers are annealed by incubating the scaffold at 135° C. for 96 hours and quenched with ice water prior to seeding with a cell. In any of the embodiments described herein, the annealing time can be varied, however, the annealing step must occur below the melting temperature of the material.

In certain additional embodiments, the scaffold demonstrates polarity in one or more planes such as through a gradient in, for example, fiber diameter, fiber composition, pore size, concentration of chemical or growth factor cues or a combination thereof. By varying the polarity of the scaffold directional growth or polarized cell growth may be enhanced.

In certain aspects the scaffold matrix, and/or fibers additionally comprise an exogenous protein or compound to promote cell growth, differentiation, and/or repair, including for example, growth factors, chemokines, polysaccharides, glycans, or the like. In any of the embodiments described herein, the polymer fiber, matrix, and/or scaffold may additionally include one or more growth factors. In certain embodiments, the growth factor to be included is capable of enhancing or further promoting cell growth and/or differentiation of the differentiable stem/progenitor cell into a mature cell phenotype. For example, in one exemplary embodiment, the cell to be seeded is an isolated differentiable neuronal progenitor cell, and a suitable growth factor to be included comprises nerve growth factor (NGF), brain-derived neurotrophic factor or a combination thereof. In any of the embodiments described herein, the growth factor may be associated to at least one of the polymeric fiber, matrix, and/or scaffold through a covalent interaction, a non-covalent interaction or a combination of both.

In certain aspects of the invention, the differentiable cell matures or differentiates within and/or on the scaffold. The differentiation status of a cell can be determined by assessing suitable phenotypic markers, e.g., cell surface proteins, and/or gene expression profiles, which are specific for a differentiated cell. In one embodiment, the mature cell phenotype comprises a neuronal cell phenotype. The mature neuronal cell phenotype is demonstrated by at least one of increased tubulin expression, reduced expression of nestin, neurite growth or a combination thereof. The mature cell phenotype can be detected using any suitable method or assay, e.g., immunoglobulin or PCR-based methods, including ELISA, Western Blot, Northern Blot, RTQ-PCR, chemiluminescence/FACS cell sorting or a combination thereof. Suitable molecular biological and biochemical techniques for assaying for the phenotype of a cell are known in the art and are described in, for example, Ausubel, et al., CURRENT PROTOCOLS IN MOLECULAR BIOLOGY, John Wiley & Sons, New York, N.Y., 1993; Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In an additional aspect, the invention provides the electroactive structure for growing isolated differentiable cell described herein comprise a three dimensional matrix of fibers comprising a biocompatible synthetic piezoelectric polymeric material, wherein the matrix of fibers is seeded with a combination of at least one isolated differentiable cell and a matrix producing or supporting cell, for example, a fibroblast, wherein the structure forms a supporting scaffold for growing/differentiating the isolated differentiable cell. In certain embodiments, the isolated differentiable cell is a differentiable neuronal stem/progenitor cell or cell capable of being differentiated into a nerve cell. In certain additional embodiments, the matrix producing or supporting cell to be included comprises a fibroblast, a glial cell, a satellite cell, a Schwann cell or a combination thereof, wherein the combination stimulates differentiation of the isolated differentiable neuronal stem/progenitor cell into a mature neuronal cell phenotype on the structure.

The polymeric scaffolds provided by the invention are generated or fabricated in order to more closely mimic the structure of the natural extracellular matrix in order to promote growth and differentiation of the seeded cell and to facilitate transplantation and/or implantation of the scaffold or cells grown on the same. For example, experimental results have demonstrated for certain exemplary embodiments, enhanced neuronal progenitor cell differentiation and neurite extension on PVDF-TrFe meshes. Also, cells on aligned nanofiber scaffolds extend neurites unidirectionally, parallel with the aligned and/or annealed fibers.

Therefore, in another aspect, described herein are methods for promoting and/or enhancing the growth and/or differentiation of a differentiable stem/progenitor cell, e.g., a neuronal stem/progenitor cell, comprising seeding a differentiable stem/progenitor cell on a scaffold comprised of an electrospun polymer that demonstrates piezoelectric properties, wherein the scaffold promotes the growth and/or differentiation of the differentiable stem/progenitor cell. In certain embodiments, the electrospun piezoelectric polymer is a polyvinyl polymer or co-polymer for example, a permanently piezoelectric poly (vinylidene fluoride trifluoroethylene) (PVDF-TrFE) copolymer. In certain embodiments, the differentiable stem/progenitor cell is a neuronal stem/progenitor cell or cell capable of being differentiated into a mature nerve cell type. In an additional embodiment, the fibers are substantially aligned and/or annealed.

In other aspects, the invention provides a method of making an implantable electroactive scaffold. In an exemplary embodiment, the method comprises the steps of (a) isolating differentiable stem/progenitor cell from a donor subject; (b) preparing a three-dimensional matrix of fibers formed of a biocompatible synthetic piezoelectric polymeric material to form a cell scaffold; (c) seeding the cell scaffold with the isolated differentiable stem/progenitor cell; and (d) growing the differentiable stem/progenitor cell on the cell scaffold so that the differentiable stem/progenitor cell differentiates into a mature cell phenotype on the scaffold. In a preferred embodiment, the differentiable stem/progenitor cell is a neuronal stem/progenitor cell or a cell capable of being differentiated into a mature nerve cell, e.g., a peripheral nerve, a CNS or spinal cord nerve. In certain embodiments, the subject is a mammal, for example a human. In an additional embodiment, the biocompatible synthetic piezoelectric polymeric material in step (b) is poly(vinylidene fluoride trifluoroethylene) copolymer. In any embodiment of this aspect, the three dimensional matrix of fibers may be formed of a biocompatible synthetic piezoelectric polymeric material by electrospinning. Further still, in any embodiment described herein, the three dimensional matrix of fibers is a non-woven mesh of nanofibers, microfibers or a combination of both. In still further embodiments, the fibers are aligned and/or annealed.

In another aspect, the invention provides methods of repairing a damaged neuronal cell or tissue in a subject. An exemplary embodiment of this aspect comprises the steps of (a) isolating at least one differentiable stem/progenitor cell from a donor subject; (b) preparing a three-dimensional matrix of fibers formed of a biocompatible synthetic piezoelectric polymeric material to form a cell scaffold; (c) seeding the cell scaffold with the isolated differentiable stem/progenitor cell; (d) growing the isolated differentiable stem/progenitor cell on the cell scaffold ex vivo or in vitro; and (e) implanting the scaffold comprising the differentiable stem/progenitor cell at the site of injury, wherein the differentiable stem/progenitor cell differentiates into a mature cell phenotype on the scaffold. In certain embodiments, the differentiable stem/progenitor cell fully differentiates on the scaffold in vivo.

In a preferred embodiment, the differentiable stem/progenitor cell is a neuronal stem/progenitor cell or a cell capable of being differentiated into a mature nerve cell, e.g., a peripheral nerve, a CNS or spinal cord nerve. In certain embodiments, the subject is a mammal, for example a human. In an additional embodiment, the biocompatible synthetic piezoelectric polymeric material in step (b) is poly(vinylidene fluoride trifluoroethylene) copolymer. In any embodiment of this aspect, the three dimensional matrix of fibers may be formed of a biocompatible synthetic piezoelectric polymeric material by electrospinning. Further still, in any embodiment described herein, the three dimensional matrix of fibers is a non-woven mesh of nanofibers, microfibers or a combination of both. In still further embodiments, the fibers are aligned and/or annealed.

The following examples are put forth so as to provide those of ordinary skill in the art with a complete disclosure and description of how to make and use the present invention, and are neither intended to limit the scope of what the inventors regard as their invention nor they intended to represent that the experiments below are all or the only experiments performed

EXAMPLES

Materials and methods useful for practicing the present invention may be further described in one or more of the following: U.S. Pat. No. 6,689,166; and U.S. Pat. No. 6,790,528; and U.S. Published Pat. App. Nos. 2004-0018226; 2006-0204539; 2009-0325296; 2009-0028921; and 2006-0128012, the disclosures of which are all incorporated herein by reference in their entirety for all purposes.

In one exemplary embodiment, an electrospun fibrous scaffold of piezoelectric polyvinylidene fluoride-trifluoroethylene (PVDF-TrFE) was evaluated. It was surprisingly and unexpectedly discovered that the piezoelectric scaffold enhanced neurite extension. Therefore, the present invention provides novel compositions and methods for treating/repairing nerve damage, including treating/repairing spinal cord injury (SCI). An aligned fibrous piezoelectric scaffold was also investigated in order to provide physical cues (via contact guidance) and local electrical activity to promote neuronal differentiation and neurite extension. Rat pheochromocytoma (PC12) and dorsal root ganglion explants (DRGs) were cultured on random or aligned fibrous PVDF-TrFE scaffolds. Neurites of PC12 cells were observed to extend and proliferated along the direction of the aligned fibers. Neurite extension of DRGs was observed on both random and aligned electrospun PVDF-TrFE scaffolds which would be advantageous to spinal cord repair.

Fabrication of Piezoelectric Tissue Engineering Scaffolds

The present invention makes use of fibers formed from a permanently piezoelectric poly(vinylidene fluoride trifluoroethylene) (PVDF-TrFE) copolymer. The PVDF-TrFE copolymer was fabricated into a nanofibrous scaffold using an electrospinning technique.

The electrospinning process is affected by varying the electric potential, flow rate, solution concentration, capillary-collector distance, diameter of the needle, and ambient parameters like temperature. PVDF-TrFE and PLLA were electrospun into fibers according to commonly used optimization procedures whereby porosity, surface area, fineness and uniformity, diameter of fibers, and the pattern thickness of the sheet could be manipulated. See, e.g., Greiner, A. et al Angew Chem. Int. Ed. Engl. 46: 5670 (2007).

The electrospinning setup used herein is described in U.S. patent application Ser. No. 11/291,701, which is incorporated herein by reference. It is comprised a syringe pump containing a 13-20 gauge needle mounted on a robotic arm in order to control the splaying of fibers on the collector. An electrically grounded stainless steel plate of dimensions 15×30 cm is used as the collector.

PVDF-TrFE copolymer (65/35) purchased from Solvay Solexis, Inc. (NJ, USA) was dissolved in Methylethylketone (MEK). For the successful formation of fibers, a 15% w/v solution concentration of the polymer in MEK was used. The syringe pump was filled with the polymer solution, and a constant flow rate of 0.035 ml/min was maintained using the syringe pump. The positive output lead of a high voltage power supply (Gamma High Voltage, Inc.) was attached to a 20 gauge needle, and a 25 kvolt voltage was applied to the solution. The collector-to-needle distance was 18.5 cm. The electrospinning process was performed in about 12% to about 13% humidity at 25 degrees C. When the charge of the polymer at increasing voltage exceeded the surface tension at the tip of the needle, the polymer splayed randomly as fibers. These were collected as nonwoven mats on the grounded plate.

Example 2

Characterization of the Electrospun PVDF-TrFE Fibers

Structure and piezoelectric activity were examined by differential scanning calorimetry (DSC), thermogravimetric analysis (TGA), thermally stimulated current (TSC) spectroscopy, X-ray diffraction (XRD) and fourier transform infrared spectroscopy (FTIR). Comparisons were made between PVDF-TrFE polymer powder and electrospun PVDF-TrFE fibers.

The fiber diameter of electrospun PVDF-TrFE fibers was characterized using Scanning Electron Microscopy (SEM) according to established methods and compared to poly L-lactic acid (PLLA) meshes. FIG. 1 shows that the resulting fibrous meshes had an average fiber diameter of 970±480 nm, with uniform fiber morphologies having no beading, as characterized by scanning electron microscopy. The fiber mats were free of droplets.

Thermally stimulated current (TSC) spectroscopy is widely used to understand dielectric relaxation in complex solid systems. TSC is based on the ability of polar molecules to be moved by an electric static field. At a temperature Tp, an electric field is applied during a time tp long enough to let the dipoles orient themselves. This configuration is fixed by a rapid decrease in temperature to reach a temperature T0. At T0, the sample is short-circuited during a time t0 to remove the space charges and to equilibrate the temperature. The progressive and sequential release of the entities oriented previously can be observed during a linear rise in temperature. The depolarization current is then recorded as a function of the temperature.

Figure 2:
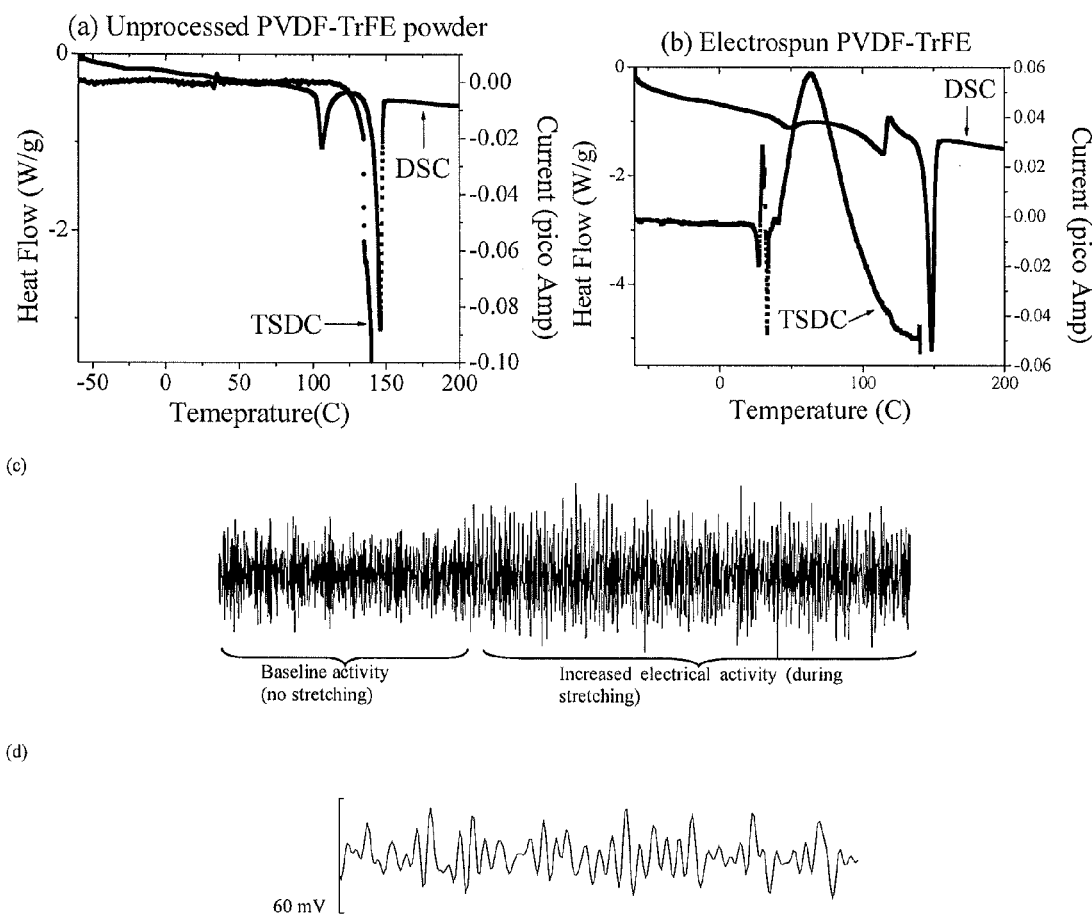
FIG. 2 depicts DSC (heat flow) and TSDC (current) results for unprocessed powder (a) and electrospun PVDF-TrFE (b). Electric response of PVDF-TrFE scaffold (c) when initializing deformation and (d) 25ms duration while deforming.

TSC measurements confirmed that the electrospun PVDF-TrFE fiber scaffolds have internal charges comparable to the original piezoelectric polymer powder. The electrospun and powder forms were heated from −60° C. to 140° C. (7 C per min) and were subjected to an externally applied field of 100 V. FIG. 2 shows the data resulting from TSC analysis of the electrospun PVDF-TrFE mat and the non-processed powder form. It shows that for both the powder and electrospun forms, there was polarization due to the applied electric field followed by a spontaneous relaxation.

Thermal Gravimetric Analysis (TGA) was performed to detect any remaining solvent in the nanofiber mat using a Thermal Gravimetric Analyzer (TA Instrument model Q50). The analyzer measures weight changes in materials with regard to temperature, which allows for the effective quantitative analysis of thermal reactions that are accompanied by mass changes resulting from dehydration, decomposition and oxidation of a sample.

The nanofiber mat was subjected to vacuum prior to the analysis. A sample of the test material was placed into a high alumina cup supported on, or suspended from, an analytical balance located outside the furnace chamber. The balance was zeroed, and the sample cup heated according to a predetermined thermal cycle. The balance sends the weight signal to the computer for storage, along with the sample temperature and the elapsed time. The TGA curve plots the TGA signal, converted to percent weight change, on the Y-axis against the reference material temperature on the X-axis.

The results showed that fibrous meshes with vacuum treatment had a 0.5% solvent content as demonstrated by a loss of 0.5 weight percent as compared to the unprocessed/raw polymer.

Results obtained by DSC, XRD and FTIR showed that the electrospinning process did not alter significantly the polymer structure compared to the original piezoelectric polymer powder.

Differential scanning calorimetry (DSC) is used to study the thermal behavior of polymers. In this technique, separate chambers for the sample and reference are heated equally. Transformations taking place in the sample are detected by the instrument, which compensates by changing the heat input so that there is a zero temperature difference between the reference and sample. The amount of electrical energy supplied to the heating elements is then proportional to the heat released by the sample. Thermal analysis was performed with a TA Model Q100 Differential Scanning Calorimeter.

Fourier-Transform Infrared Spectroscopy (FTIR) is used to observe vibrational changes in chemical bonds. Here, infrared radiation in the range from 4000 to 600 cm$^{-1}$, the mid-infrared region, was used. The presence and intensity of specific vibrational frequencies allows for determination of functional groups in organic molecules. The class of material (proteinaceous, cellulosic, and so forth) then can be identified from these functional groups.

A micro x-ray diffractometer capable of focusing a collimated x-ray beam (20 to 800 micron diameter range) onto areas of interest within the sample was used to generate an x-ray diffraction (XRD) pattern characteristic for the crystalline phases contained within the sample. X-rays diffracted by the sample strike a detector and are converted to an electronic signal that is then further processed by software. Search-match software then was used to match the unknown diffraction pattern to a database of diffraction patterns collected from reference compounds.

The degree of crystallinity was determined, and the piezoelectric crystal form of the copolymer present in the electrospun PVDF-TrFE mats was confirmed, by DSC. Comparisons of PVDF-TrFE mats with the piezoelectric unprocessed powder and solvent-cast film as well as with nonpiezoelectric-unpoled PVDF pellets were made.

TABLE 1

Comparison of DSC data with literature values

| Physical form | PVDF Pellet | PVDF-TrFE (65/35) Powder | PVDF-TrFE (65/35) Solvent-cast film | PVDF-TrFE (65/35) Electrospun fiber |
|---|---|---|---|---|
| Tm (C) | 171 (161*) | 107 (1 peak) | 115 (1 peak) | 115 (1 peak) |
|  |  | 147 (154.55**) (2 peak) | 147 (2 peak) | 149 (2 peak) |
| ΔHf (J/g) | 45 (50*) | 13 (1 peak) | 13 (1 peak) | 15 (1 peak) |
|  |  | 23 (30**) (2 peak) | 34 (2 peak) | 28 (2 peak) |

*Zhao, Z. et al., J. Appl. Polym. Sci. 97: 466-74 (2005);
**Data provided by supplier (Solvay Solexis, Inc.)

Table 1, which compares the experimental DSC data with literature values for test polymers (in parentheses), shows that low and high temperature peaks were observed in the PVDF-TrFE polymer during the first and second heating cycle. The differences in the first heating cycle between the test polymers were not detectable in the second heating cycle, which suggests that there is no chemical degradation or changes in the chemical structure due to the fabrication process. The melting points and heats of fusion for PVDF-TrFE materials are distinct from values obtained for the unpoled PVDF pellet, indicating that the piezoelectric beta-phase crystal form is present in the electrospun mat.

Moreover, the electrospun electroactive PVDF-TrFE fibers of the present invention do not require poling to show a piezoelectric effect. The term "poling" as used herein refers to the adjustment of the polarity of a substance. For example, electric dipoles may be aligned (meaning arranged, positioned or synchronized in a manner that allows for proper or optimal functioning) by utilizing an electric field. In this contect, the term "polarity" refers to the property, state or condition of having or manifesting two opposite or opposing charges within the same body (versus, e.g., cellular polarity, which refers to a situation in which a cell has two or more anatomically and/or functionally distinct cellular domains).

Example 3

PVDF-TrFE Fiber Mats Support Stem Cells

Three studies were conducted to establish that the PVDF-TrFE fiber mesh can be used as a scaffold to support stem cells or other cell types Materials and Methods
1. Cells
(a) Cell line model for neuronal differentiation. When treated with nerve growth factor (NGF), PC12 cells, a cell line derived from a pheochromocytoma of the rat adrenal medulla, stop dividing, grow long neurites, and undergo terminal differentiation, which makes this cell line a useful model system for neuronal differentiation.

PC12 cells (ATCC number CRL-1721) were seeded at $3 \times 10^3$ cells per $cm^2$ culture dish and maintained in ATCC formulated F-12K medium containing 1.5% fetal bovine serum and 15% horse serum. Cultures were maintained at 37° C., 95% air, 5% $CO_2$ atmosphere. For induction of the neuronal phenotype, 50 ng/ml NGF (Chemicon) was added to the medium at the start of the culture and maintained throughout the duration of the culture. The term "induction media" refers to the medium containing NGF.

(b) Fibroblasts. Normal human skin fibroblasts (ATCC number SCRC-1041) were seeded at $5 \times 10^3$ cells per $cm^2$ culture dish and maintained in Dulbecco's modified Eagle's medium containing 15% fetal bovine serum.

(c) Mesenchymal stem cells. Human mesenchymal stem cells (hMSCs) were prepared as described in Livingston, et al., *J. Materials Science: Materials in Med.* 14: 211-218 (2003) and in U.S. Pat. No. 5,486,359, which are incorporated herein by reference. In brief, bone marrow aspirates of 30-50 mL were obtained from healthy human donors. Marrow samples were washed with saline and centrifuged over a density cushion of ficoll. The interface layer was removed, washed, and the cells counted. Nucleated cells recovered from the density separation were washed and plated in tissue culture flasks in Dulbecco's Modified Eagle's Medium (DMEM) containing 10% fetal bovine serum ("FBS", HyClone Laboratories, Inc.). Non-adherent cells were washed from the culture during biweekly feedings. Colony formation was monitored for a 14-17 day period. MSC's were passaged when the tissue culture flasks were near confluent. At the end of the first passage, MSCs were enzymatically removed from the culture flask using trypsin-EDTA and replated at a lower density for further expansion. At the end of the second passage, MSC's were either seeded onto scaffolds or cryopreserved until future use. The hMSC cells were identified as multipotent stem cells based on surface marker characterization, which distinguishes the stem cells from other cell types in the bone marrow, for example white blood cells. Cells expressing CD44 (CD44+) and the absence of CD45 (CD45−) and CD34 (CD34−) surface antigens were verified by fluorescence-activated-cell-sorter.

Chondrogenic differentiation of hMSCs was performed according to published procedures. See Barry, F. et al., *Exp. Cell Res.* 268, 189 (2001), which is incorporated herein by reference. $2 \times 10^5$ cells were seeded on PVDF-TrFE scaffolds in 24-well plates using three different culture media: (i) the chondrogenic culture media containing TGFβ3, or induction media, (CCM+), consisted of 1 mM sodium pyruvate (Sigma), 0.1 mM ascorbic acid-2-phosphate (Wako), $1 \times 10^{-7}$ M dexamethasone (Sigma), 1% ITS 1 (Collaborative Biomedical Products), and 10 ng/ml recombinant human TGβ3 (Oncogene Sciences) dissolved in Dulbecco's Modified Eagle's Medium containing 4-5 g/L glucose (DMEM-LG), (ii) chondrogenic culture media (CCM) without TGFβ3 (CCM−); (iii) mesenchymal stem cell growth media (MSCGM), the standard growth media for hMSCs, consisting of DMEM-LG with 10% fetal bovine serum and 1% antibiotic-antimycotic. Cells were harvested after 1, 14, and 28 days of culture.

Cell pellet cultures served as controls for these experiments. A single cell pellet was produced by centrifuging $2.5 \times 10^5$ cells in a 15 mL centrifuge tube and culturing the pelleted cells in the tube.

Cell viability: Metabolic activity and cell growth were measured using the XTT kit (Biotium, USA). XTT is a tetrazolium derivative that measures cell viability based on the activity of mitochondria enzymes in live cells that reduce XTT and are inactivated shortly after cell death. XTT is reduced to a highly water-soluble orange colored product, the amount of which is proportional to the number of living cells in the sample, and can be quantified by measuring absorbance at wavelength of 475 nm.

Cells were plated onto scaffolds in 96-well tissue culture plates at 10,000 cells per well for up to 7 days. Reagents were added such that the final volume of tissue culture medium (containing 10% FBS) in each well was 0.1 ml. For one 96-well plate, 25 μl Activation Reagent was mixed with 5 ml XTT Solution to derive activated XTT solution. 25 μl or 50 μl of the activated XTT solution was added to each well and the plate incubated in an incubator for 4 hours. The plate was shaken gently to evenly distribute the dye in the wells. The absorbance of the samples was measured spectrophotometrically at a wavelength of 450-500 nm. Reference absorbance is measured at a wavelength of 630-690 nm.

Real time reverse transcriptase-polymerase chain reaction (RT-PCR): RNA was isolated using a Qiagen Mini kit (Qiagen). Samples were lysed and then homogenized using QiaShredder columns (Qiagen). Ethanol was added to the lysate and the lysate was loaded onto the RNeasy silica-gel membrane. Pure, concentrated RNA then was eluted from the membrane in water.

Relative gene expression analysis (QuantiTect SYBR Green RT-PCR kit, Qiagen) for chondrogenic markers (chondroadherin, type II collagen), and focal adhesion kinase (FAK) was performed using the MX4000 detection system (Stratagene). Ribosomal protein, large, PO ("RPLPO") was used as housekeeping gene.

Qiagen PCR kit: 2× QuantiTect SYBR Green RT-PCR Master Mix (stored at −20° C.), template RNA, primers, and RNase-free water were thawed, mixed individually and placed on ice. A reaction components master mix was prepared as follows:

| Component | Volume/reaction | Final concentration |
| --- | --- | --- |
| 2x QuantiTect SYBR Green RT-PCR Master Mix | 12.5 μl | 1x |
| Primer A | Variable | 0.5-2.0 μM |
| Primer B | Variable | 0.5-2.0 μM |
| QuantiTect RT Mix | 0.25 μl | 0.25 μl |
| RNAse-free water | Variable | — |
| Optional: Uracil-N-glycolase, heat labile | Variable | 1-2 units/reaction |
| Template RNA | Variable | ≤500 ng/reaction |
| Total volume | 25 μl | |

Where final reaction volumes other than 25 μl were used, the volumes of 2.times. Quanti-Tect SYBR Green RT-PCR Master Mix and Quanti Tect RT Mix used were adjusted so that the ratio between them remained constant.

The master mix was mixed thoroughly and appropriate volumes dispensed into PCR tubes. Template RNA (≤500 ng/reaction) was added to the individual PCR tubes and incubated on ice for less than 30 min. The MX4000 was programmed and data acquisition performed during the extension step. A melting curve analysis of the RT-PCR product(s) between 55° C. and 95° C. was performed to verify specificity and identify of the RT-PCR products.

A standard curve was generated using various RNA concentrations, which contain substantial levels of chondrogenic markers (chondroadherin, type II collagen) and focal adhesion kinase (FAK). Two optical channels, one for SYBR Green and one for a reference dye (ROX), were used to correct for volume and plate location differences. Each template was analyzed in triplicate. Stratagene reaction tubes (Cat. No. 41002) and caps (Cat. No. 410024) were used, and fluorscence data was collected for SYBR Green. A typical thermal profile used was the following: 50° C. for 30 min (reverse transcriptase step), 95° C. for 15 min (to activate the DNA polymerase), 40 cycles of: 94° C. for 15 sec, 55° C. for 30 sec, 72° C. for 30 sec (triplicate readings of fluorescence were taken during this phase of the cycle.)

A dissociation curve was generated after the amplification cycles were completed. For the amplification plots, fluorescence was analyzed as "dRn" to generate C.sub.t values for all of the samples simultaneously. Gene expression levels were analyzed according to Mueller (Mueller, P. Y., Janoviak, H., Miserez, A. R., Dobbie, Z., *Biotechniques* 32, 1372-74 (2002)), which is incorporated herein by reference, and expressed as "mean normalized expression."

Confocal fluorescence microscopy was used to obtain fluorescence images of cells cultured on fiber scaffolds. A fluorescent stain, which visualizes nuclear DNA (4',6-diamidino-2-phenylindole, DAPI, Invitrogen, USA) and the actin cytoskeleton (Alexa Fluor 488 phalloidin; Invitrogen, USA) in fixed cells was used. Fluorescence images of cells cultured on fiber scaffolds were taken with a confocal fluorescence microscope (Clsi, Nikon, Japan).

Cell proliferation. Cell number over time was measured using the PicoGreen assay (Invitrogen).

sGAG synthesis: Absorbance at 656 nm was used to measure total sulfated proteoglycan content ("sGAG") using the Blycan assay (Biodyne Science, UK).

Results. The results show that PDVF-TrFE fiber piezoelectric scaffolds are biocompatible and stimulate differentiation of hMSCs into chondrocytes, PC-12 neuronal cells into neurites; and stimulate attachment and growth of fibroblasts on the PVDF-TrFE scaffold as compared to growth of these cells under normal culture conditions.

Figure 3A:
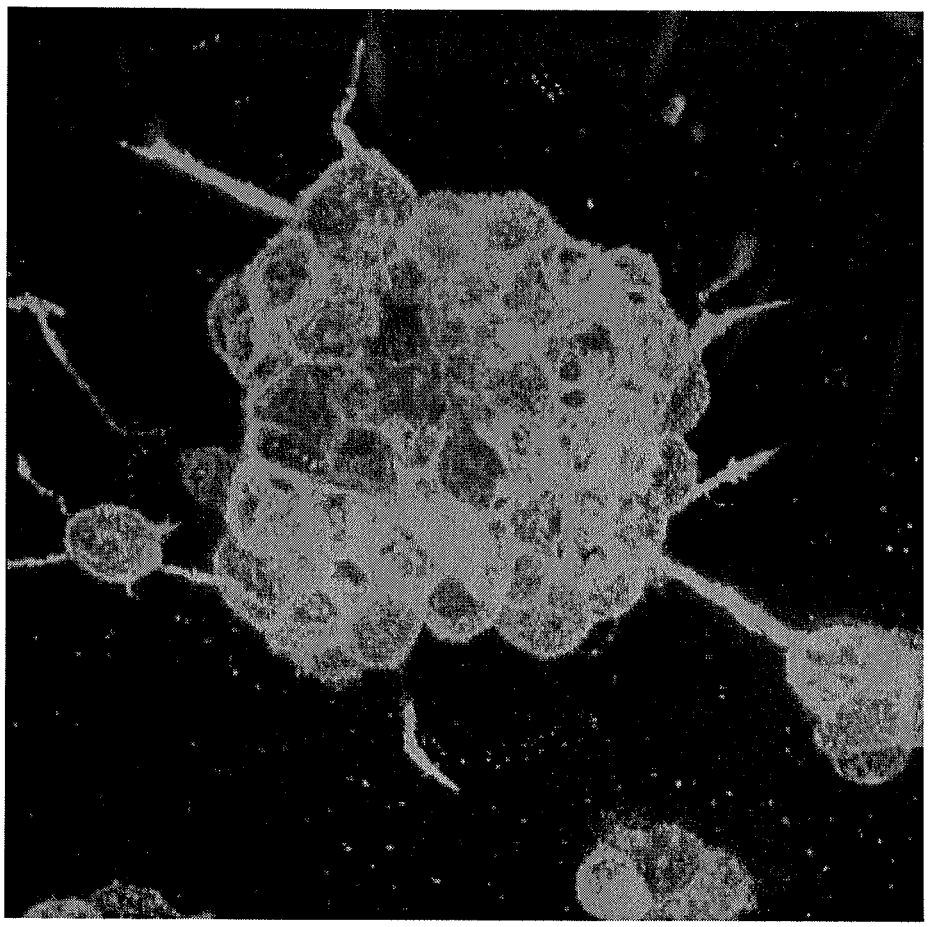
FIG. 3 shows confocal images of PC-12 cells cultured on (a) PVDF-TrFE meshes in induction media; (b) in standard growth media; and (c) PC-12 cells on PLLA meshes in induction media (60× objective D); and metabolic activity of PC-12 cells at 10 days in culture *$P<0.05$ for PVDF-TrFE versus collagen.
Figure 3B:
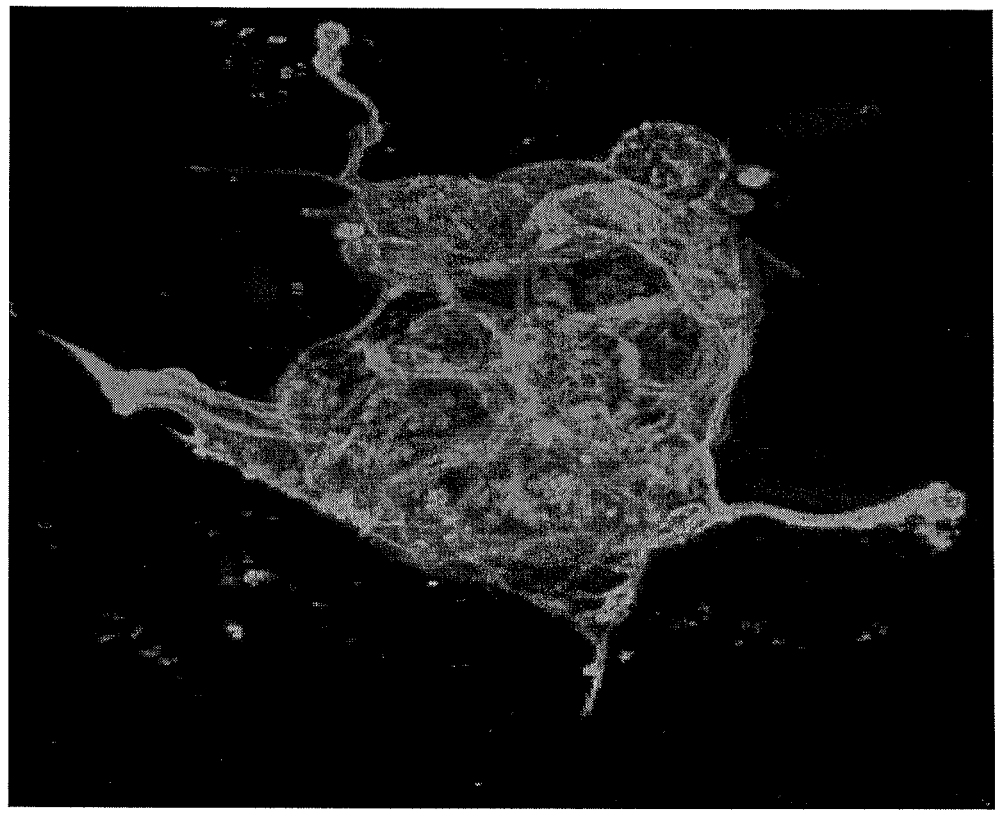
Figure 3C:
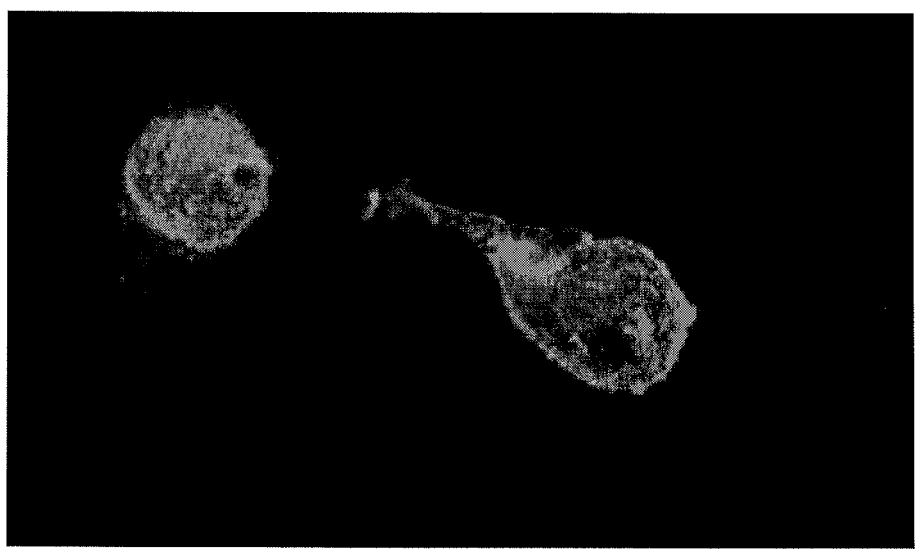
Figure 3D:
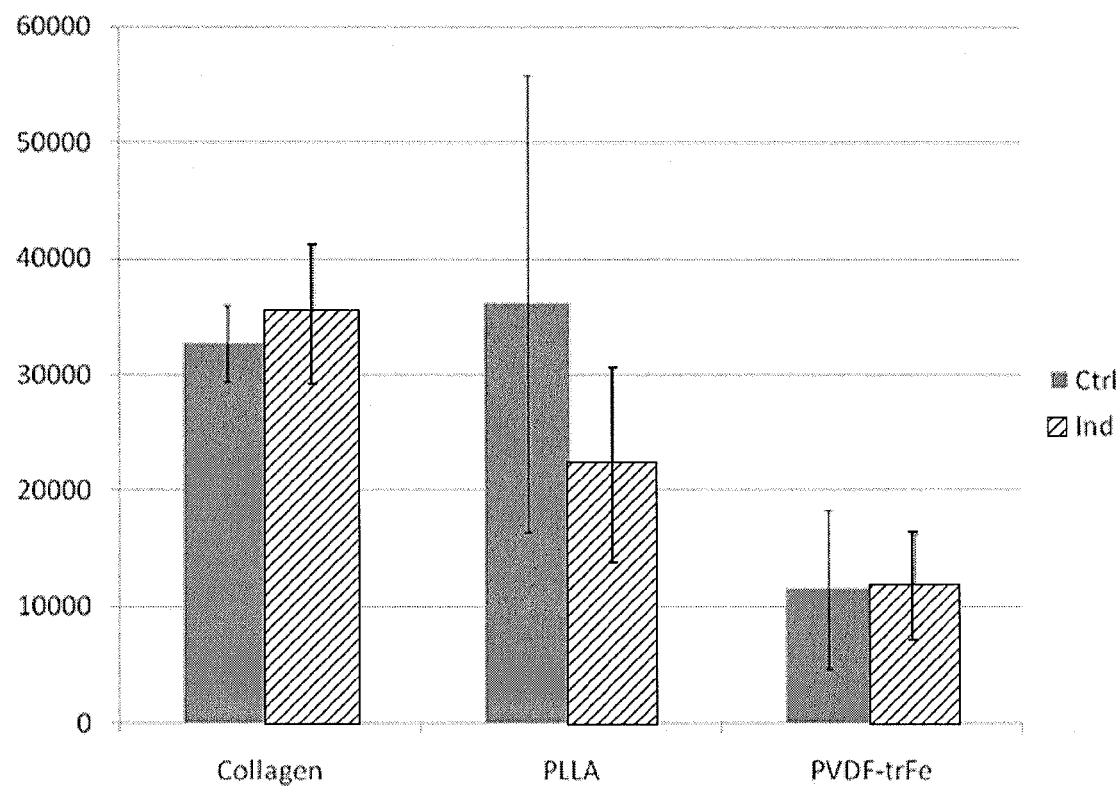

FIGS. 3a-3c shows that at 10 days in culture, extensive neurite extension on PVDF-TrFE meshes was seen with or without media containing Nerve Growth Factor (NGF). Neurite extension of cells grown on electrospun poly-L-lactic acid [PLLA] (average fiber diameter of 1.0±0.4 μm) scaffolds appeared less extensive and only occurred in the presence of NGF. As shown in FIG. 5d, cell growth, as measured by metabolic activity using the XTT kit (Biotium, USA), was significantly lower on PVDF-TrFE meshes for both growth and induction media as compared to tissue culture polystyrene and PLLA scaffolds, suggesting that PVDF-TrFE downregulates proliferation and facilitates differentiation.

Figure 4:
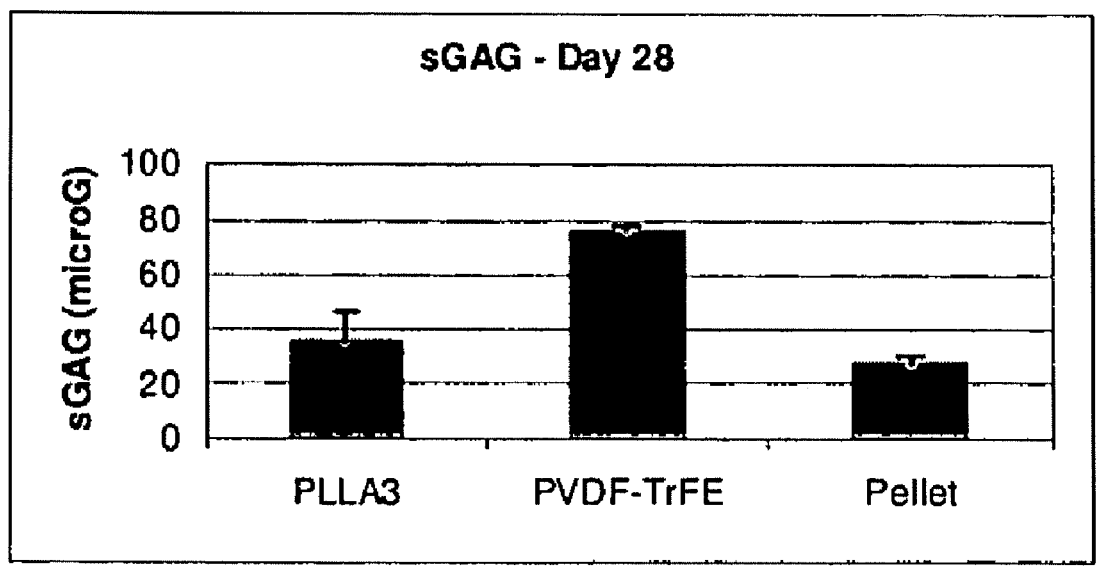
FIG. 4 shows chondroadherin and focal adhesion kinase (FAK) gene expression in human mesenchymal stem cells (hMSCs) cultured for 28 days on PLLA and PVDF-TrFE scaffolds. Cell pellet cultures serve as controls.
Figure 5:
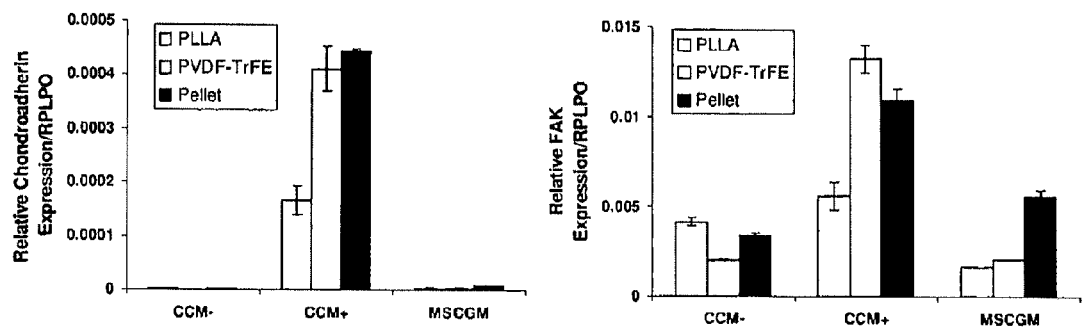
FIG. 5 shows glycosaminoglycan production (sGAG) for human mesenchymal stem cells cultured in chondrogenic induction media on PLLA and PVDF-TrFE meshes at 28 days. Pellet cultures served as a positive control. *$p<0.05$.

FIGS. 4 and 5 shows that for human mesenchymal stem cell chondrogenesis, glycosaminoglycan production by cells on PVDF-TrFE meshes/mats was significantly higher than for cells on PLLA or in pellet culture (positive control) in inductive media. It is known that transforming growth factor .beta. (TGF-.β) induces chondrogenesis in hMSCs and involves deposition of a cartilage-specific extracellular matrix. Barry, F. et al., *Exp. Cell Res.* 268, 189 (2001). Initial studies showed that chondrogenic markers and sGAG synthesis was significantly induced by CCM+ media. As shown in FIG. 4, the sGAG concentrations and chondroadherin/FAK gene expression was significantly higher on PVDF-TrFE as compared to PLLA scaffolds (p<0.01). However, no significant differences between PVDF-TrFE and PLLA scaffolds could be seen using CCM− and MSCGM media (chondroadherin, type II collagen, and FAK gene expression; sGAG synthesis).

Human skin fibroblasts (ATCC number SCRC-1041) were cultured on PVDF-TrFE fiber scaffolds over a 7-day period. Tissue culture polystyrene (TCPS) served as the control).

Figure 6:
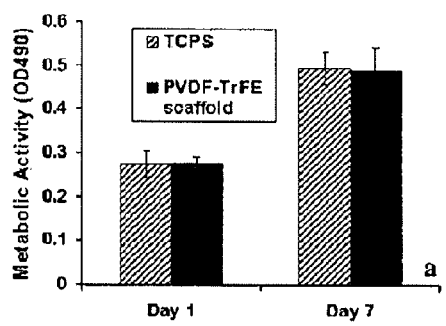
FIG. 6 shows (a) viability and growth of human skin fibroblasts on electrospun PVDF-TrFE fiber scaffold compared to tissue culture polystyrene (TCPS); (b) SEM image of electrospun PVDF-TrFE fibers.
Figure 6:
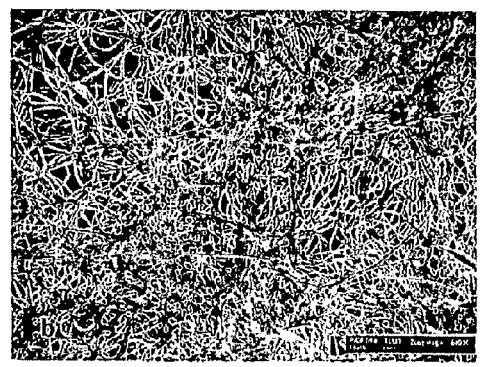
Figure 7:
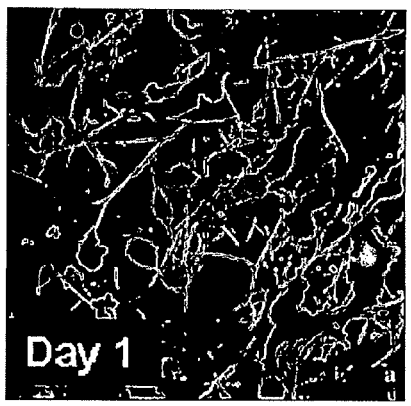
FIG. 7 shows confocal scanning laser microscopy images of human skin fibroblasts attached to PVDF-TrFE fibers after 1 day and after 7 days of cell culture.
Figure 7:
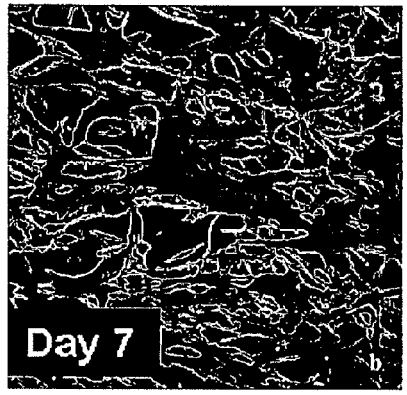

FIG. 6 and FIG. 7 show that fibroblasts grew and were well-spread on PVDF-TrFE meshes. This was comparable to growth on tissue culture plastic (positive control).

Confocal fluorescence microscopy verified the attachment and proliferation of the cells on the PVDF-TrFE fiber scaffolds. FIG. 7 shows confocal scanning laser microscopy images of human skin fibroblasts attached to PVDF-TrFE fibers after 1 day and after 7 days of cell culture. The cell morphologies of one day cultures on the fiber scaffolds are distinctly different from those of 7-day cultures. On day 1, the cells are not fully spread out. When grown on the scaffolds for a longer time (7 days) cells exhibit a more elongated and spread-out morphology.

Example 4

PC12 and DRG Culture

For one embodiment of the present invention the scaffolds were pre-conditioned in cell culture media for one day prior to seeding. PC12 cells were seeded at $0.18 \times 10^6$ cells/cm$^2$ on to the scaffolds and collagen coated plates (control) and were cultured in either control media or induction media containing neural growth factor (NGF, 250 ng/mL) a day after. PC12 cells were stained with Phalloidin (cytoskeletal stain, Invitrogen) and proliferation was evaluated by MTT cell proliferation assay (Invitrogen) at day 10 and 14.

In an exemplary embodiment of the present invention, DRGs isolated from E15 embryonic rat pup were plated on the scaffolds and stained with Vybrant® CFDA SE cell tracker (Invitrogen, Carlsbad, Calif.) at day 3.

Average fiber diameter in this exemplary embodiment of electrospun PVDF-TrFE was 0.75 μm±0.08. Directional fiber orientation was observed in the aligned scaffolds (FIG. 1). Crystallization (data not shown) and melting point of electrospun PVDF-TrFE (148.1° C.) were shifted to a higher temperature as compared to the unprocessed powder (146.1° C.) (FIG. 2). Current movement occurred just before melting in the unprocessed powder (FIG. 2a). Current movement started at 65° C. and continued before the melting in temperature of electrospun PVDF-TrFE (FIG. 2b). The 35° C. peak is the spontaneous relaxation of the Teflon sheets. When the mechanical deformation started, an increase in electric response occurred (FIG. 2c). Amplitude of response varied between −30 mV to 30 mV (FIG. 2d) for this embodiment of the present invention.

Figure 8:
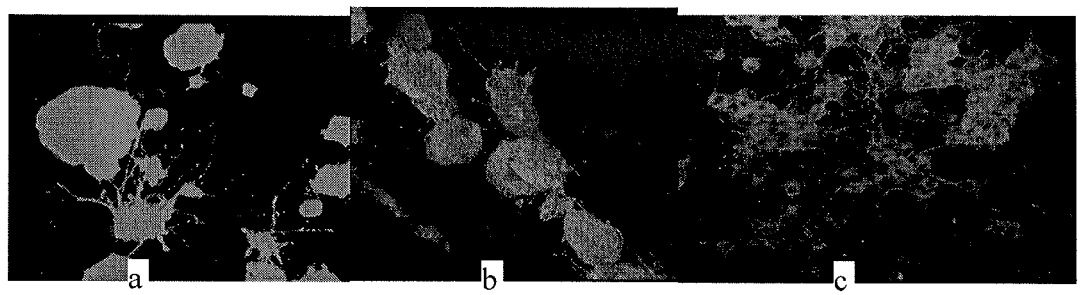
FIG. 8 depicts PC12 cells stained with Phalloidin on random (a) or aligned (b) PVDF-TrFE and collagen (c) in induction media (20×). (d) MTT viability assay for PC12 cells on random PVDF-TrFE and collagen in induction media. Cell proliferation on collagen was higher than PVDF-TrFE ($p>0.05$)
Figure 8:
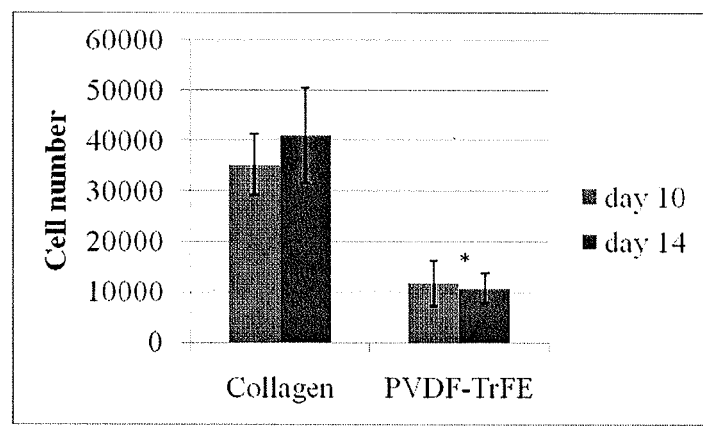
Figure 9:
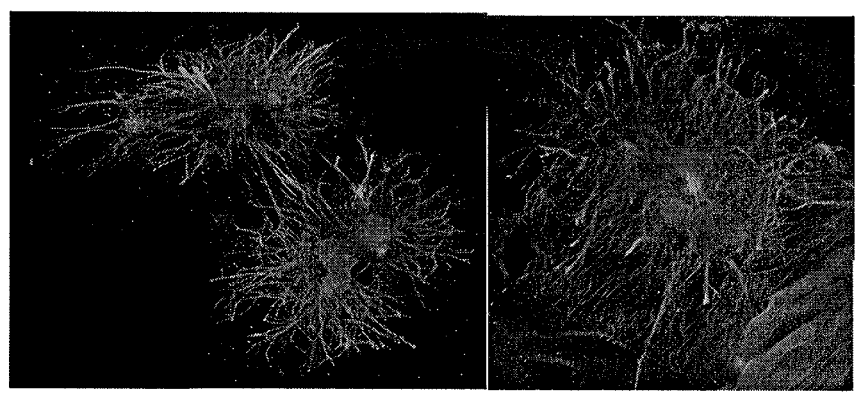
FIG. 9 depicts DRGs stained with Vybrant® CFDA SE cell tracker at day 3 on random (left) and aligned (right) PVDF-TrFE scaffolds (4×)

PC12 neurite extension was observed on both random and aligned scaffolds (FIG. 8b,d). Neurite extension both occurred along the direction of alignment (FIG. 8d) and on the collagen coated plates (FIG. 8f). PC12 proliferation was higher on collagen in the induction group on both days 10 and 14 (FIG. 8g). Proliferation in the control media was similar for both materials at both time points (data not shown). Neurite extension of DRGs was also observed on both random and aligned PVDF-TrFE scaffolds (FIG. 9).

In certain exemplary embodiments of the present invention, DSC results of unprocessed and electrospun PVDF-TrFE indicated no significant alternation occurred during the electrospinning process, as indicated by similar melting temperatures. Shifting of melting and crystallization temperature suggested extended chain crystallization during the electrospinning process. The piezoelectric phenomenon is characterized by the presence of dipole crystal structure. For certain embodiments, dipole movement would occur upon heating and could be observed as the current movement on TSDC. DSC and TSDC results of electrospun PVDF-TrFE (FIG. 2b) suggested a phase transform allowing dipole movement. Crystal structure movement upon melting contributed to the current movement in the unprocessed PVDF-TrFE powder (FIG. 2a). The electrical activity detected in these embodiments while deforming the electrospun PVDF-TrFE (FIG. 2c,d) corresponded to the observation of its piezoelectric properties.

PC12 cell proliferated and extended neurites along the direction of fiber alignment indicated the influence of contact guidance. No difference in cell proliferation was observed in control media on both days suggesting it may due to the differentiation process.

Figure 10:
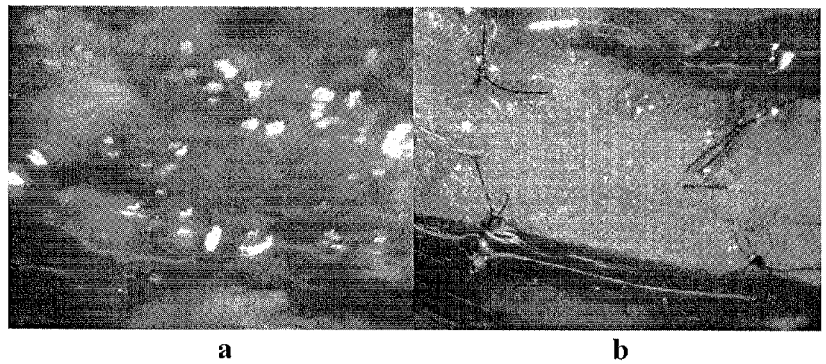
FIG. 10 depicts an Image of contused spinal cord in the rat a) after contusion and b) after the insertion of the PVDF-TrFE scaffold.

Neurite extension of both PC12 cells and DRGs was observed on both random and aligned electrospun PVDF-TrFE scaffolds, suggesting its utility as a scaffold for spinal cord repair. The piezoelectric scaffolds can be implanted in contusion or transection spinal cord injury (SCI) models (FIG. 10). We are currently evaluating the scaffold seven days after contusion injury to evaluate the effect of this intervention. The contusion injury model in rats is routinely used to mimic human SCI. (21) A 200 kilodyne (kd) (1dyne=10 uN) contusion spinal cord injury can be inducted using an infinite horizon impactor. At one week post-injury, the spinal cords will be re-exposed in all animals and scaffold constructs will be inserted into the contused area of the cords. Functional recovery can be evaluated histologically and by motor and sensory function.

Example 5

Figure 11:
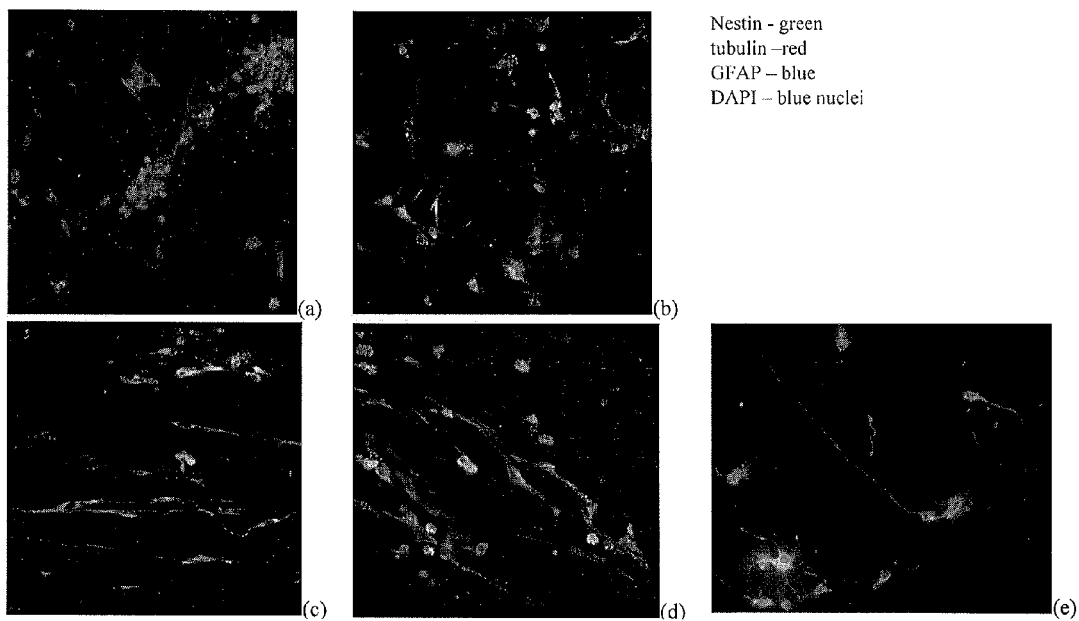
FIG. 11 Confocal microscopy images of hNPCs on PVDF-TrFE-L a) random, b) random-annealed, c) aligned, d) aligned-annealed (all at 40× obj), and e) laminin (20× obj.)
Figure 12:
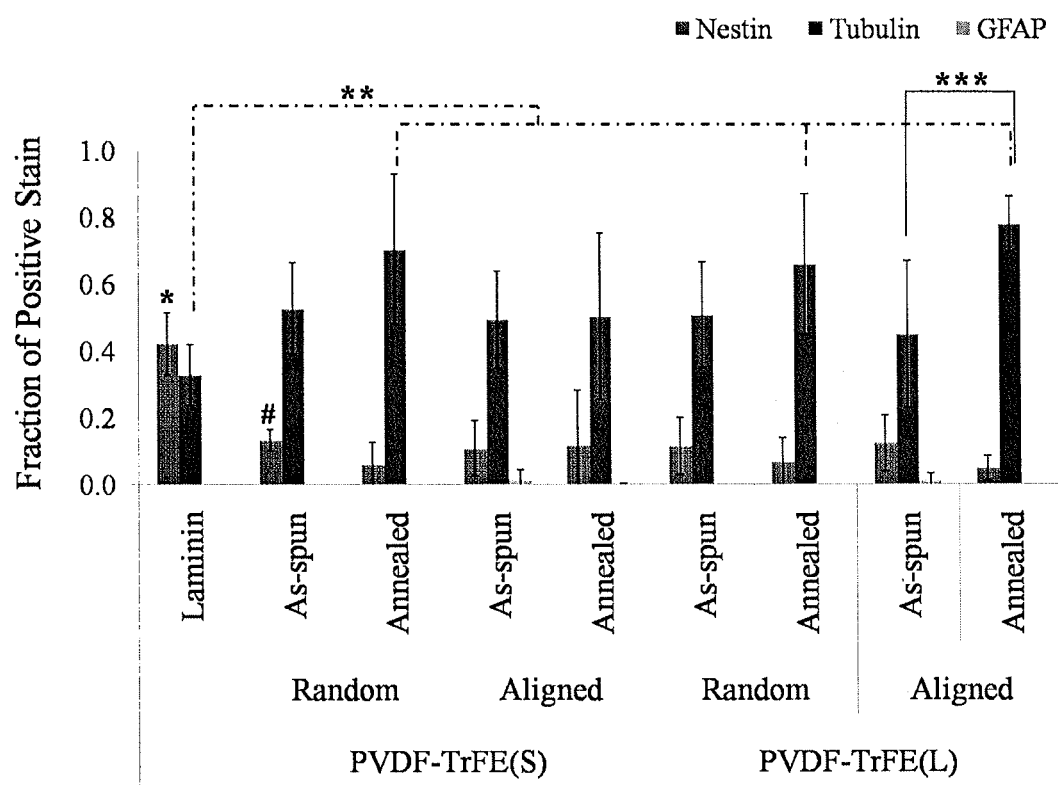
FIG. 12 Fraction of positive nestin, tubulin, and GFAP on various scaffolds. *Nestin positive cells were the highest on laminin. Tubulin positive cells were the lowest on laminin in comparison to annealed, random and aligned PVDF-TrFE (L) and annealed random PVDF-TrFE(S). *Tublin positive cells on annealed, aligned PVDF-TrFE(L) was significantly greater than as-spun aligned PVDF-TrFE(L). Very little GFAP positive cells could be detected in all of the samples.

Evaluation of Neural Differentiation of Human Neural Stem/Progenitor Cells on Piezoelectric Scaffolds (with reference to FIGS. 11 and 12).

This study investigates the neural differentiation of human neural stem/progenitor cells (hNPCs) on fibrous, PVDF-TrFE to determine its potential use as a scaffold in nerve repair. The piezoelectric properties of PVDF-TrFE were enhanced by annealing to increase crystal organization. Comparisons were made with laminin coated tissue culture plastic (control).

Scaffold Fabrication (electrospinning): Polymer solutions for electrospinning were prepared with PVDF-TrFE in methyl-ethyl-ketone (MEK) Random and aligned electrospun scaffolds were collected on a plate and a rotating drum, respectively. Annealed samples were kept at 135° C. for 96 hours and quenched with ice water.

Characterization of Thermal and Piezoelectric Properties Evaluation. Scanning electron microscopy (SEM) images were taken to evaluate the fiber diameter and orientation. Differential scanning calorimetry (DSC) was used to evaluate thermally active transition such as melting temperature. X-ray diffraction (XRD) was performed to evaluate crystal structure of as-spun and annealed PVDF-TrFE. Thermally-stimulated current (TSC) was used to confirm piezoelectricity by measuring the current indicating the dipole movement in response to an increase in temperature. In exemplary embodiments, thermal and piezoelectric properties were evaluated using differential scanning calorimetry (DSC) and thermal stimulated depolarization current (TSDC) on both unprocessed powder and electrospun PVDF-TrFE. A heat-cool-heat cycle from −60° C. to 200° C. with heating and cooling ramp of 7° C./min was used on DSC to evaluate thermally active transition such as crystallization, melting, and phase transition. Electrospun PVDF-TrFE or the powder was sandwiched between the two Teflon films and heated from −60° C. to 140° C. for TSDC experiments [6].

Electric Response.

Electrodes (10 mm×10 mm) were attached to the ends of the scaffold using silver conductive epoxy for one embodiment of the present invention. The scaffold of this inventive embodiment was mechanically deformed at the rate of 10 mm/min using Instron. The electrodes were then connected to a custom-made amplifier circuit and the signals were recorded using Matlab.

In Vitro Study:

hNPCs (Lonza), which are cryopreserved neurospheres obtained from fetal brain tissue (20 weeks), were seeded at 45,000 cells/cm$^2$ and cultured in differentiation media (Lonza) with 25 ng/mL brain-derived neurotrophic factor (BDNF) or standard growth media for 9 days. Comparisons were made with laminin coated plates. The cells were fixed and stained with anti-Nestin (NPCs), glial fibrillary acidic protein (GFAP) (astrocytes), and neuron-specific beta-III tubulin (neuron), followed by DAPI as counter stain. 4 images were taken for each sample (n=6 per group) and positive stain was manually counted to obtain percentage of differentiation. One-way analysis of variance (ANOVA) and Tukey-Kramer test were used to determined the statistic significance between the groups ($p<0.05$).

Results.

The average fiber diameter of micron-(L) and sub-micron-(S) PVDF-TrFE were 3.32±0.2 µm and 0.75±0.08 µm, respectively. The melting point of as-spun of PVDF-TrFE (L) and (S) increased from 147.9° C. and 147.8° C. to 152.4° C. and 154.5° C. after annealing, respectively. The increase in melting temperature suggested an increase in crystallinity due to annealing. XRD results indicated an increase in the intensity of the piezoelectric beta phase at 20.4° and the loss of the non-piezoelectric alpha phase around 18.5° on the annealed in comparison to the as-spun samples. The annealing process induced crystal organization hence, enhancing the piezoelectric properties.

This study demonstrates the potential for using an electroactive scaffold as described herein for nervous tissue repair. The scaffolds enhanced neural differentiation, as indicated by a lower level of nestin positive cells on scaffolds in comparison to laminin surfaces. Neuronal differentiation may be enhanced on annealed scaffolds, which display higher piezoelectricity, as indicated by the higher fraction of cells expressing beta-III tubulin.

Although the systems and methods of the present disclosure have been described with reference to exemplary embodiments thereof, the present disclosure is not limited thereby. Indeed, the exemplary embodiments are implementations of the disclosed systems and methods are provided for illustrative and non-limitative purposes. Changes, modifications, enhancements and/or refinements to the disclosed systems and methods may be made without departing from the spirit or scope of the present disclosure. Accordingly, such changes, modifications, enhancements and/or refinements are encompassed within the scope of the present invention.

REFERENCES

The following references are incorporated herein by reference in their entirety for all purposes.
(1) N. Zhang, H. Yan, X. Wen, "Tissue-engineering approaches for axonal guidance," *Brain Res Brain Res Rev*, vol 49, pp. 48-64, 2005.
(2) R. B. Borgens, "Electric Fields in Vertebrate Repair" in *Natural and Applied Voltage in Vertebrate Regeneration and Healing*, Wiley-Liss, 1989.
(3) N. B. Patel, M. M. Poo, "Perturbation of the direction of neurite growth by pulsed and focal electric fields," *Journal of Neurosci*, vol 4, pp 2939-47, 1984.
(4) R. Valentini, "Electrically charged polymeric substrates enhance nerve-fiber outgrowth in vitro," *Biomaterials*, vol 13, pp. 183-90, 1992.
(5) A. J. Lovinger, "Ferroelectric Polymers," *Science*, vol 220, pp 1115-21, 1983.
(6) L. H. Catalani, G. Collins, M. Jaffe, "Evidence for molecular orientation and residual charge in the electrospinning of poly (butylenes terephthalate) nanofibers," *Macromolecules*, vol 40, pp. 1693-7, 2007.
(7) Kim Y, Haftel V K, Kumar S, Bellamkonda R V. The role of aligned polymer fiber-based constructs in the bridging of long peripheral nerve gaps. Biomaterials 2008; 29(21): 3117-27.
(9) Borgens R B. Electrically mediated regeneration and guidance of adult mammalian spinal axons into polymeric channels. Neuroscience 1999; 91(1):251-64.
(10) Shapiro S, Borgens R, Pascuzzi R, Roos K, Groff M, Purvines S, et al. Oscillating field stimulation for complete spinal cord injury in humans: a phase 1 trial. Journal of Neurosurgery Spine 2005; 2(1):3-10.
(11) Himes B T, Neuhuber B, Coleman C, Kushner R, Swanger S A, Kopen G C, et al. Recovery of function following grafting of human bone marrow-derived stromal cells into the injured spinal cord. Neurorehabilitation and Neural Repair 2006; 20:278-96.
(12) Cummings B J, Uchida N, Tamaki S J, Salazar D L, Hooshmand M, Summers R, et al. Human neural stem cells differentiate and promote locomoter recovery in spinal cord-injured mice. Proceedings of the National Academy of Sciences 2005; 102(39):14069-74.
(13) Cizkova D, Rosocha J, Vanicky I, Jergova S, Cizek M. Transplants of human mesenchymal stem cells improve functional recovery after spinal cord injury in the rat. Cellular and Molecular Neurobiology 2006; 26(7/8):1167-80.
(14) N.S.C.I.A. Spinal cord injury fact sheet. Birmingham; 2001.
(15) Yannas I V. Tissue and organ regeneration in adults. Springer; 2001.
(16) Brook G A, Lawrence J M, Raisman G. Columns of Schwann cells extruded into the CNS induce in-growth of astrocytes to form organized new glial pathways. Glia 2001; 33:118-30.
(17) Oudega M, Xu X M. Schwann cell transplantation for repair of the adult spinal cord. Journal of Neurotrauma 2006; 23(3-4):453-67.
(18) Negishi H. Optic nerve regeneration within artificial Schwann cell graft in the adult rat. Brain Research Bulletin 2001; 55:409-19.
(19) Lankford K L, Sasaki M, Radtke C, Kocsis J D. Olfactory ensheathing cells exhibit unique migratory, phagocytic, and myelinating properties in the X-irradiated spinal cord not shared by Schwann cells. Glia 2008; epub ahead of print.
(20) Desawa M. Specific induction of neuronal cells from bone marrow stromal cells and application for autologous transplantation. Journal of Clinical Investigation 2004; 113:1701-10.
(21) Rosenzweig E S, McDonald J W. Rodent models for treatment of spinal cord injury: research trends and progress toward useful repair. Current Opinion in Neurology 2004; 17(2):121-31.

We claim:

1. A method for growing and differentiating a neural cell or tissue in a subject comprising the steps of (a) isolating at least one differentiable neural cell from a donor subject; (b) preparing a three-dimensional matrix of electrospun fibers formed of a biocompatible synthetic permanently piezoelectric polymeric material to form a cell scaffold; (c) annealing, either thermally or chemically, the electrospun fibers, wherein after annealing the fibers demonstrate enhanced piezoelectric characteristics, crystal organization or a combination of both; (d) seeding the cell scaffold with the isolated differentiable neural cell; (e) growing the isolated differentiable neural cell on the cell scaffold ex vivo or in vitro; and (f) implanting the scaffold comprising the differentiable neural cell, wherein the differentiable neural cell differentiates into a mature neural cell phenotype on the scaffold.

2. The method of claim 1, wherein the differentiable neural cell fully differentiates on the scaffold in vivo.

3. The method according to claim 1, wherein the biocompatible synthetic permanently piezoelectric polymeric material in step (b) is poly(vinylidene fluoride trifluoroethylene) copolymer.

* * * * *